United States Patent
Hauber et al.

(10) Patent No.: US 10,150,953 B2
(45) Date of Patent: Dec. 11, 2018

(54) WELL-TOLERATED AND HIGHLY SPECIFIC TAILORED RECOMBINASE FOR RECOMBINING ASYMMETRIC TARGET SITES IN A PLURALITY OF RETROVIRUS STRAINS

(71) Applicants: HEINRICH-PETTE-INSTITUT LEIBNIZ-INSTITUT FÜR EXPERIMENTELLE VIROLOGIE-STIFTUNG BÜRGERLICHEN RECHTS, Hamburg (DE); TECHNISCHE UNIVERSITÄT DRESDEN, Dresden (DE)

(72) Inventors: Joachim Hauber, Hamburg (DE); Jan Chemnitz, Oederquar (DE); Frank Buchholz, Dresden (DE); Janet Karpinski, Dresden (DE)

(73) Assignees: Heinrich-Pette-Institut Leibniz-Institut für Experimentelle Virologie-Stiftung bürgerlichen Rechts, Hamburg (DE); Technische Universität Dresden, Dresden (DE)

(*) Notice: Subject to any disclaimer, the term of this patent is extended or adjusted under 35 U.S.C. 154(b) by 43 days.

(21) Appl. No.: 15/317,088

(22) PCT Filed: Sep. 1, 2015

(86) PCT No.: PCT/EP2015/069890
§ 371 (c)(1),
(2) Date: Dec. 7, 2016

(87) PCT Pub. No.: WO2016/034553
PCT Pub. Date: Mar. 10, 2016

(65) Prior Publication Data
US 2017/0175091 A1 Jun. 22, 2017

(30) Foreign Application Priority Data

Sep. 2, 2014 (EP) .................... 14183277

(51) Int. Cl.
*C12N 9/12* (2006.01)
*C12N 1/20* (2006.01)
(Continued)

(52) U.S. Cl.
CPC .............. *C12N 9/1241* (2013.01); *C12N 9/22* (2013.01); *C12N 15/1058* (2013.01); *A61K 38/00* (2013.01)

(58) Field of Classification Search
None
See application file for complete search history.

(56) References Cited

U.S. PATENT DOCUMENTS 6,262,341 B1   7/2001   Baszczynski et al.
6,890,726 B1   5/2005   Sauer et al.
(Continued)

FOREIGN PATENT DOCUMENTS

WO     02/44409 A2       6/2002
WO   2005/081632 A2      9/2005
(Continued)

OTHER PUBLICATIONS

Studer. Residue mutations and their impact on protein structure and function: detecting beneficial and pathogenic changes. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — Seed IP Law Group LLP

(57) ABSTRACT

The present invention relates to a method for preparing an expression vector encoding a well-tolerated and highly (Continued)

specific tailored recombinase, which tailored recombinase is capable of recombining asymmetric target sequences within the long terminal repeat (LTR) of proviral DNA of a plurality of retrovirus strains which may be inserted into the genome of a host cell, as well as to the obtained expression vector, cells transfected with these, expressed recombinase and pharmaceutical compositions comprising the expression vector, cells and/or recombinase. Pharmaceutical compositions are useful, e.g., in treatment and/or prevention of retrovirus infection, in particular, HIV infection. In particular, the invention relates to well-tolerated and highly specific tailored recombinases capable of combining asymmetric target sequences in a more than 90% of HIV-strains, thereby excising the HIV-1 sequences, and expression vectors encoding them.

17 Claims, 7 Drawing Sheets

Specification includes a Sequence Listing.

(51) Int. Cl.

| | |
|---|---|
| *C12N 15/00* | (2006.01) |
| *C07H 21/04* | (2006.01) |
| *C12P 21/06* | (2006.01) |
| *C12P 21/04* | (2006.01) |
| *C12N 9/22* | (2006.01) |
| *C12N 15/10* | (2006.01) |
| *A61K 38/00* | (2006.01) |

(56) References Cited

U.S. PATENT DOCUMENTS

| | | |
|---|---|---|
| 7,112,715 B2 | 9/2006 | Chambon et al. |
| 8,871,516 B2 | 10/2014 | Hauber et al. |
| 2006/0014264 A1 | 1/2006 | Sauer et al. |
| 2009/0217400 A1 | 8/2009 | Carmi et al. |
| 2013/0164271 A1 | 6/2013 | Hauber et al. |
| 2015/0104433 A1 | 4/2015 | Hauber et al. |
| 2017/0130212 A1 | 5/2017 | Hauber et al. |

FOREIGN PATENT DOCUMENTS

| | | |
|---|---|---|
| WO | 2008/083931 A1 | 7/2008 |
| WO | 2009/007982 A1 | 1/2009 |
| WO | 2011/147590 A2 | 12/2011 |

OTHER PUBLICATIONS

Abremski et al., "Bacteriophage P1 Site-specific Recombination: Purification and Properties of the Cre Recombinase Protein," *The Journal of Biological Chemistry* 259(3):1509-1514, 1984.

Abremski et al., "Studies on the Properties of P1 Site-Specific Recombination: Evidence for Topologically Unlinked Products following Recombination," *Cell* 32(4):1301-1311, 1983.

Adachi et al., "Production of Acquired Immunodeficiency Syndrome-Associated Retrovirus in Human and Nonhuman Cells Transfected with an Infectious Molecular Clone," *Journal of Virology* 59(2):284-291, 1986.

Alper et al., "Tuning genetic control through promoter engineering," *Proceedings of the National Academy of Sciences of the United States of America* 102(36):12678-12683, 2005. (8 pages).

Altschul et al., "Gapped BLAST and PSI-BLAST: a new generation of protein database search programs," *Nucleic Acids Research* 25(17):3389-3402, 1997.

Beyer et al., "Oncoretrovirus and Lentivirus Vectors Pseudotyped with Lymphocytic Choriomeningitis Virus Glycoprotein: Generation, Concentration, and Broad Host Range," *Journal of Virology* 76(3):1488-1495, 2002.

Blackard et al., "Transmission of Human Immunodeficiency Type 1 Viruses with Intersubtype Recombinant Long Terminal Repeat Sequences," *Virology* 254(2):220-225, 1999.

Bloom et al., "Evolving strategies for enzyme engineering," *Current Opinion in Structural Biology* 15(4):447-452, 2005.

Buchholz et al., "Alteration of Cre recombinase site specificity by substrate-linked protein evolution," *Nature Biotechnology* 19(11):1047-1052, 2001.

Buchholz et al., "Different thermostabilities of FLP and Cre recombinases: implications for applied site-specific recombination," *Nucleic Acids Research* 24(21):4256-4262, 1996.

Buchholz et al., "Improved properties of FLP recombinase evolved by cycling mutagenesis," *Nature Biotechnology* 16(7):657-662, 1998.

Chemnitz et al., "Excision of HIV-1 Proviral DNA using Tre-Recombinase: An Experimental Update," *Antiviral Research* 86(1):A31-A32, 2010.

Chiu et al., "Cellular APOBEC3G restricts HIV-1 infection in resting $CD4^+$ T cells," *Nature* 435(7038):108-114, 2005.

Chun et al., "Early establishment of a pool of latently infected, resting $CD4^+$ T cells during primary HIV-1 infection," *Proceedings of the National Academy of Sciences of the United States of America* 95(15):8869-8873, 1998.

Coates et al., "Site-directed genome modification: derivatives of DNA-modifying enzymes as targeting tools," *Trends in Biotechnology* 23(8):407-419, 2005.

Collins et al., "Engineering proteins that bind, move, make and break DNA," *Current Opinion in Biotechnology* 14(4):371-378, 2003.

Combes et al., "The *Streptomyces* Genome Contains Multiple Pseudo-attB Sites for the φC31-Encoded Site-Specific Recombination System," *Journal of Bacteriology* 184(20):5746-5752, 2002.

Crameri et al., "DNA shuffling of a family of genes from diverse species accelerates directed evolution," *Nature* 391(6664):288-291, 1998.

Derossi et al., "Cell Internalization of the Third Helix of the Antennapedia Homeodomain is Receptor-independent," *The Journal of Biological Chemistry* 271(30):18188-18193, 1996.

Derossi et al., "The Third Helix of the Antennapedia Homeodomain Translocates through Biological Membranes," *The Journal of Biological Chemistry* 269(14):10444-10450, 1994.

Donovan et al., "The end of the beginning for pluripotent stem cells," *Nature* 414(6859):92-97, 2001.

Donzella et al., "AMD3100, a small molecule inhibitor of HIV-1 entry via the CXCR4 co-receptor," *Nature Medicine* 4(1):72-77, 1998.

Dybul et al., "Guidelines for Using Antiretroviral Agents among HIV-Infected Adults and Adolescents," *Annals of Internal Medicine* 137(5; Part 2):381-434, 2002.

Eddy, "Profile hidden Markov models," *Bioinformatics Review* 14(9):755-763, 1998.

Edelman et al., "Synthetic promoter elements obtained by nucleotide sequence variation and selection for activity," *Proceedings of the National Academy of Sciences of the United States of America* 97(7):3038-3043, 2000.

Elliott et al., "Intercellular Trafficking and Protein Delivery by a Herpesvirus Structural Protein," *Cell* 88(2):223-233, 1997.

Emerman et al., "HIV-1 Regulatory/Accessory Genes: Keys to Unraveling Viral and Host Cell Biology," *Science* 280(5371):1880-1884, 1998.

Fawell et al., "Tat-mediated delivery of heterologous proteins into cells," *Proceedings of the National Academy of Sciences of the United States of America* 91(2):664-668, 1994.

Finzi et al., "Identification of a Reservoir for HIV-1 in Patients on Highly Active Antiretroviral Therapy," *Science* 278(5341):1295-1300, 1997.

Flowers et al., "Inhibition of Recombinant Human Immunodeficiency Virus Type 1 Replication by a Site-Specific Recombinase," *Journal of Virology* 71(4):2685-2692, 1997.

Fraser et al., "Reduction of the HIV-1-infected T-cell reservoir by immune activation treatment is dose-dependent and restricted by the potency of antiretroviral drugs," *AIDS* 14(6):659-669, 2000.

(56) References Cited

OTHER PUBLICATIONS

GenBank, "*Salmonella enterica* subsp. enterica serovar Newport str. SL317 gcontig_1106632477151, whole genome shotgun sequence," Accession No. NZ_ABEW01000015, Fricke et al., URL=http://www.ncbi.nlm.nih.gov/nuccore/156105548?report=genbank, download date Feb. 25, 2013, 14 pages.

GenBank, "*Shewanella* sp. ANA-3 plasmid 1, complete sequence," Accession No. CP000470, Copeland et al., URL=http://www.ncbi.nlm.nih.gov/nuccore/CP000470, download date Feb. 25, 2013, 120 pages.

Gulick et al., "Treatment with Indinavir, Zidovudine, and Lamivudine in Adults with Human Immunodeficiency Virus Infection and Prior Antiretroviral Therapy," *The New England Journal of Medicine* 337(11):734-739, 1997.

Guzman et al., "Tight Regulation, Modulation, and High-Level Expression by Vectors Containing the Arabinose $P_{BAD}$ Promoter," *Journal of Bacteriology* 177(14):4121-4130, 1995.

Hartenbach et al., "A Novel Synthetic Mammalian Promoter Derived From an Internal Ribosome Entry Site," *Biotechnology and Bioengineering* 95(4):547-559, 2006.

Hauber et al., "Identification of cellular deoxyhypusine synthase as a novel target for antiretroviral therapy," *The Journal of Clinical Investigation* 115(1):76-85, 2005.

Hazuda et al., "Integrase Inhibitors and Cellular Immunity Suppress Retroviral Replication in Rhesus Macaques," *Science* 305(5683):528-532, 2004.

Hoess et al., "Mechanism of Strand Cleavage and Exchange in the Cre-lox Site-specific Recombination System," *Journal of Molecular Biology* 181(3):351-362, 1985.

Indian Office Action, dated Nov. 18, 2014, for Indian Application No. 4814/DELNP/2009, 3 pages.

Johannes et al., "Directed evolution of enzymes and biosynthetic pathways," *Current Opinion in Microbiology* 9(3):261-267, 2006.

Karpinski et al., "Directed evolution of a recombinase that excises the provirus of most HIV-1 primary isolates with high specificity," *Nature Biotechnology* 34(4):401-409, 2016. (28 pages).

Kim et al., "Characterization of Cre-loxP Interaction in the Major Groove: Hint for Structural Distortion of Mutant Cre and Possible Strategy for HIV-1 Therapy," *Journal of Cellular Biochemistry* 80(3):321-327, 2001.

Koresawa et al., "Synthesis of a New Cre Recombinase Gene Based on Optimal Codon Usage for Mammalian Systems," *Journal of Biochemistry* 127(3):367-372, 2000.

Krasnow et al., "Site-Specific Relaxation and Recombination by the Tn3 Resolvase: Recognition of the DNA Path between Oriented res Sites," *Cell* 32(4):1313-1324, 1983.

Kulkosky et al., "HAART-Persistent HIV-1 Latent Reservoirs: Their Origin, Mechanisms of Stability and Potential Strategies for Eradication," *Current HIV Research* 4(2):199-208, 2006.

Lalezari et al., "Enfuvirtide, an HIV-1 Fusion Inhibitor, for Drug-Resistant HIV Infection in North and South America," *The New England Journal of Medicine* 348(22):2175-2185, 2003. (12 pages).

Lee et al., "A Novel Mutant loxP Containing Part of Long Terminal Repeat of HIV-1 in Spacer Region: Presentation of Possible Target Site for Antiviral Strategy Using Site-Specific Recombinase," *Biochemical and Biophysical Research Communications* 253(3):588-593, 1998.

Lee et al., "An engineered lox sequence containing part of a long terminal repeat of HIV-1 permits Cre recombinase-mediated DNA excision," *Biochemistry and Cell Biology* 78(6):653-658, 2000.

Lehrman et al., "Depletion of latent HIV-1 infection in vivo: a proof-of-concept study," *Lancet* 366(9485):549-555, 2005.

Lewandoski, "Conditional Control of Gene Expression in the Mouse," *Nature Reviews Genetics* 2(10):743-755, 2001.

Lin et al "Enhanced cell-permeant Cre protein for site-specific recombination in cultured cells," *BMC Biotechnology* 4:25, 2004. (13 pages).

Little et al., "Antiretroviral-Drug Resistance Among Patients Recently Infected With HIV," *The New England Journal of Medicine* 347(6):385-394, 2002.

Loonstra et al., "Growth inhibition and DNA damage induced by Cre recombinase in mammalian cells," *Proceedings of the National Academy of Sciences of the United States of America* 98(16):9209-9214, 2001.

Macara, "Transport into and out of the Nucleus," *Microbiology and Molecular Biology Reviews* 65(4):570-594, 2001.

Malim et al., "Immunodeficiency virus rev trans-activator modulates the expression of the viral regulatory genes," *Nature* 335(6186):181-183, 1988.

Marcello, "Latency: the hidden HIV-1 challenge," *Retrovirology* 3(1):7, 2006. (9 pages).

Matsumura et al., "In vitro Evolution of Beta-glucuronidase into a Beta-galactosidase Proceeds Through Non-specific Intermediates," *Journal of Molecular Biology* 305(2):331-339, 2001.

Minshull et al., "Protein evolution by molecular breeding," *Current Opinion in Chemical Biology* 3(3):284-290, 1999.

Nagy, "Cre Recombinase: The Universal Reagent for Genome Tailoring," *Genesis* 26(2):99-109, 2000.

Needleman et al., "A General Method Applicable to the Search for Similarities in the Amino Acid Sequence of Two Proteins," *Journal of Molecular Biology* 48(3):443-453, 1970.

Nolden et al., "Site-specific recombination in human embryonic stem cells induced by cell-permeant Cre recombinase," *Nature Methods* 3(6):461-467, 2006.

O'Doherty et al., "Human Immunodeficiency Virus Type 1 Spinoculation Enhances Infection through Virus Binding," *Journal of Virology* 74(21):10074-10080, 2000.

Oess et al., "Novel cell permeable motif derived from the PreS2-domain of hepatitis-B virus surface antigens," *Gene Therapy* 7(9):750-758, 2000.

Pearson et al., "Improved tools for biological sequence comparison," *Proceedings of the National Academy of Sciences of the United States of America* 85(8):2444-2448, 1988.

Peitz et al., "Ability of the hydrophobic FGF and basic TAT peptides to promote cellular uptake of recombinant Cre recombinase: A tool for efficient genetic engineering of mammalian genomes," *Proceedings of the National Academy of Sciences of the United States of America* 99(7):4489-4494, 2002.

Ratner et al., "Polymorphism of the 3' open reading frame of the virus associated with the acquired immune deficiency syndrome, human T-lymphotropic virus type III," *Nucleic Acids Research* 13(22):8219-8229, 1985.

Richard et al., "Cellular Uptake of Unconjugated TAT Peptide Involves Clathrin-dependent Endocytosis and Heparan Sulfate Receptors," *The Journal of Biological Chemistry* 280(15):15300-15306, 2005.

Rüfer et al., "Non-contact positions impose site selectivity on Cre recombinase," *Nucleic Acids Research* 30(13):2764-2771, 2002.

Ruhl et al., "Eukaryotic Initiation Factor 5A is a Cellular Target of the Human Immunodeficiency Virus Type 1 Rev Activation Domain Mediating Trans-Activation," *The Journal of Cell Biology* 123(6; Part 1):1309-1320, 1993.

Sanger et al., "DNA sequencing with chain-terminating inhibitors," *Proceedings of the National Academy of Sciences of the United States of America* 74(12):5463-5467, 1977.

Santoro et al., "Directed evolution of the site specificity of Cre recombinase," *Proceedings of the National Academy of Sciences of the United States of America* 99(7):4185-4190, 2002.

Saraf-Levy et al., "Site-specific recombination of asymmetric lox sites mediated by a heterotetrameric Cre recombinase complex," *Bioorganic & Medicinal Chemistry* 14(9):3081-3089, 2006.

Sauer et al., "DNA recombination with a heterospecific Cre homolog identified from comparison of the pac-c1 regions of P1-related phages," *Nucleic Acids Research* 32(20):6086-6095, 2004.

Schambach et al., "Equal Potency of Gammaretroviral and Lentiviral SIN Vectors for Expression of $O^6$-Methylguanine-DNA Methyltransferase in Hematopoietic Cells," *Molecular Therapy* 13(2):391-400, 2006.

Scherr et al., "Gene Transfer into Hematopoietic Stem Cells Using Lentiviral Vectors," *Current Gene Therapy* 2(1):45-55, 2002.

Sclimenti et al., "Directed evolution of a recombinase for improved genomic integration at a native human sequence," *Nucleic Acids Research* 29(24):5044-5051, 2001.

(56) References Cited

OTHER PUBLICATIONS

Shehu-Xhilaga et al., "Antiretroviral Compounds: Mechanisms Underlying Failure of HAART to Eradicate HIV-1," *Current Medicinal Chemistry* 12(15):1705-1719, 2005.
Shimshek et al., "Codon-Improved Cre Recombinase (iCre) Expression in the Mouse," *Genesis* 32(1):19-26, 2002.
Smith et al., "Overlapping Genes and Information Theory," *Journal of Theoretical Biology* 91(2):379-380, 1981.
Stark et al., "Catalysis by site-specific recombinases," *Trends in Genetics* 8(12):432-439, 1992.
Stemmer, "Rapid evolution of a protein in vitro by DNA shuffling," *Nature* 370(6488):389-391, 1994.
Sternberg et al., "Bacteriophage P1 cre Gene and its Regulatory Region: Evidence for Multiple Promoters and for Regulation by DNA Methylation," *Journal Molecular Biology* 187(2):197-212, 1986.
Sternberg et al., "Bacteriophage P1 Site-specific Recombination: I. Recombination Between loxP Sites," *Journal of Molecular Biology* 150(4):467-486, 1981.
Tan et al., "Fusion Proteins Consisting of Human Immunodeficiency Virus Type 1 Integrase and the Designed Polydactyl Zinc Finger Protein E2C Direct Integration of Viral DNA into Specific Sites," *Journal of Virology* 78(3):1301-1313, 2004.
Van Duyne, "A Structural View of Cre-loxP Site-Specific Recombination," *Annual Review of Biophysics and Biomolecular Structure* 30:87-104, 2001. (24 pages).
Vivès et al., "A Truncated HIV-1 Tat Protein Basic Domain Rapidly Translocates through the Plasma Membrane and Accumulates in the Cell Nucleus," *The Journal of Biological Chemistry* 272(25):16010-16017, 1997.
Vives, "Cellular uptake [correction of utake] of the Tat peptide: an endocytosis mechanism following ionic interactions," *Journal of Molecular Recognition* 16(5):265-271, 2003.
Volkert et al., "Site-Specific Recombination Promotes Plasmid Amplification in Yeast," *Cell* 46(4):541-550, 1986.
Voziyanov et al., "Stepwise Manipulation of DNA Specificity in Flp Recombinase: Progressively Adapting Flp to Individual and Combinatorial Mutations in its Target Site," *Journal of Molecular Biology* 326(1):65-76, 2003.
Yuan et al., "Laboratory-Directed Protein Evolution," *Microbiology and Molecular Biology Reviews* 69(3):373-392, 2005.
Buchholz et al., "In vitro evolution and analysis of HIV-1 LTR-specific recombinases," *Methods* 53:102-109 (2011).
Karpinski et al., "Universal Tre (uTre) recombinase specifically targets the majority of HIV-1 isolates," *Journal of the International AIDS Society* 17(Suppl 3):19706, Poster Sessions—Abstract P174 (1 page) (2014).
Sarkar et al., "HIV-1 Proviral DNA Excision Using an Evolved Recombinase," *Science* 316:1912-1915 (Jun. 29, 2007).
Surendranath et al., "SeLOX—a locus of recombination site search tool for the detection and directed evolution of site-specific recombination systems," *Nucleic Acids Research* 38, Web Server issue:W293-W298 (Jun. 6, 2010).

* cited by examiner

Fig. 1 a) Cre                                    SEQ ID NO:6
b) Tre common consensus 100% (WO 2011/147590)   SEQ ID NO:7
c) Tre 3.0 consensus 100% (WO 2011/147590)      SEQ ID NO:8
d) Tre 3.1 consensus 85% (all clones)           SEQ ID NO:9
e) Tre 3.1 consensus 100% (3 clones)            SEQ ID NO:10
f) uTre sequence                                SEQ ID NO:11

```
                                    31
1 3    7 10 12 15       23      30          40    44        51
MSNLLTVHQNLPALPVDATSDEVRKNLMDMFRDRQAFSEHTWKMLLSVCRSWAAWCKLN a
MSXXXTXXXXLXALXXDXXSDXXXXXLXXXXRDXXAXSXXTWXXLLSXCRXWXAWCXXX b
MSXXXTXXXXLSALLXDXXSDXXXXXLXXXXRDXXAXSXXTWXVLLSXCRXWXAWCXXX c
MSXXXTLXXXLSALLXDXXSDXXXXXLXXVRDXXAXSXRTWXVLLSXCRTWXAWCXXX  d
MSXLXTLHQXLSALLVDXXSDEXRKNLMDVLRDRQAFSERTWKVLLSVCRTWAAWCXLN e
MSILLTLHQSLSALLVDATSDEARKNLMDVLRDRQAFSERTWKVLLSVCRTWAAWCKLN f 60                77          86 89  93        102     108 111
NRKWFPAEPEDVRDYLLYLQARGLAVKTIQQHLGQLNMLHRRSGLPRPSDSNAVSLVMRR a
XRXXFPXXPXXVRXYLLXLQXRGLXVXTXQQHLXXLNMXHRRXGLXRXXDXXXVSLXXRR b
XRXXFPXXPXXVRXYLLXLQXRGLXVNTXQQHLAXLNMXHRRXGLXRXXDSXXVSLXXRR c
XRXXFPXXPXXVRXYLLHLQXRGLXVNTXLQHLAXLNMXHRRXGLXRXGDSXXVSLXXRR d
NRKXFPAEPEDVRDYLLHLQXRGLXVNTXLQHLAQLNMLHRRFGLPRPGDSXAVSLVXRR e
NRKWFPAEPEDVRDYLLHLQARGLAVNTILQHLAQLNMLHRRFGLPRPGDSDAVSLVMRR f 155     163         175
122           131           147   153  160  166    174
IRKENVDAGERAKQALAFERTDFDQVRSLMENSDRCQDIRNLAFLGIAYNTLLRIAEIAR a
IRXENVDAGERXKQALAFXRXDXXXXXXLXXXSXXXXDXRXLAXLGXAYNTLLRXXEXXX b
IRXENVDAGERXKQALAFXRXDXXXXXXLXXXSXXXXDXRXLAXLGXAYNTLLRXSEXXX c
IRXENVDAGERXKQALAFXRXDXXXXXXLXXXSXXGXDXRTLAXLGXAYNTLLRXSEXXX d
IRRENVDAGERTKQALAFERTDFDQVRALMEXSXRGQDIRXLAXLGVAYNTLLRXSEIAR e
IRRENVDAGERTKQALAFERTDFDQVRALMENSERGQDIRTLALLGVAYNTLLRVSEIAR f 182           198                            232
IRVKDISRTDGGRMLIHIGRTKTLVSTAGVEKALSLGVTKLVERWISVSGVADDPNNYLF a
XRXXDXSXTXGGRXLIHXXXTKTLVSTXGVEKALSLXXTXLXERWXSXSGVAXXXXXXYLF b
XRXXDXSXTXGGRXLIHXXXTKTLVSTXGVEKALSLXXTXLXERWXSXSGVAXXXXXXYLF c
XRXXDXSXTXGGRXLIHXXXTKTLVSTXGVEKALSLXXTXLXERWXSXSGVAXXXXXXYLF d
IRXXDISRTDGGRMLIHIXRTKTLVSTAGVEKALSLGVTXLVERWISVSGVAXDPNNYLF e
IRIKDISRTDGGRMLIHISRTKTLVSTAGVEKALSLGVTKLVERWISVSGVASDPNNYLF f 244          260 263
 241      249  255 259 262  268        278
CRVRKNGVAAPSATSQLSTRALEGIFEATHRLIYGAKDDSGQRYLAWSGHSARVGAARDM a
CXXXXXGXAXPXAXXXLSXXXLXXIFXXXHXXXXGAKXXSGXRYXXWSGHSARVGAARDM b
CXXXXXGXAXPXAXXXLSXXXLXXIFXXXHXXXXGAKXXSGXRYXXWSGHSARVGAARDM c
CQXXIXGXAVPXAXXXLSXDXLRXIFXXAHXXXXGAKGSGXRYXXWSGHSARVGAARDM d
CXVRXNGXAVPSATSXLSTDVLRXIFXAAHRLXYGAKDGSGQRYLAWSGHSARVGAARDM e
CQVRINGVAVPSATSRLSTDVLRKIFEAAHRLIYGAKDGSGQRYLAWSGHSARVGAARDM f 319
300    307   317 320
ARAGVSIPEIMQAGGWTNVNIVMNYIRNLDSETGAMVRLLEDGD* a
ARAGVXIXEIMQAGGWXTVXXVMNYIRNLDSEXGAMVRLLEXXX* b
ARAGVXIAEIMQAGGWXTVXXVMNYIRNLDSEXGAMVRLLEXXX* c
ARAGVXIAEIMQAGGWXTVESVMNYIRNLDSEXGAMVRLLEXXX* d
ARAGVSIAEIMQAGGWTTVXSVMNYIRNLDSETGAMVRLLEDGD* e
ARAGVSIAEIMQAGGWTTVESVMNYIRNLDSETGAMVRLLEDGD* f
```

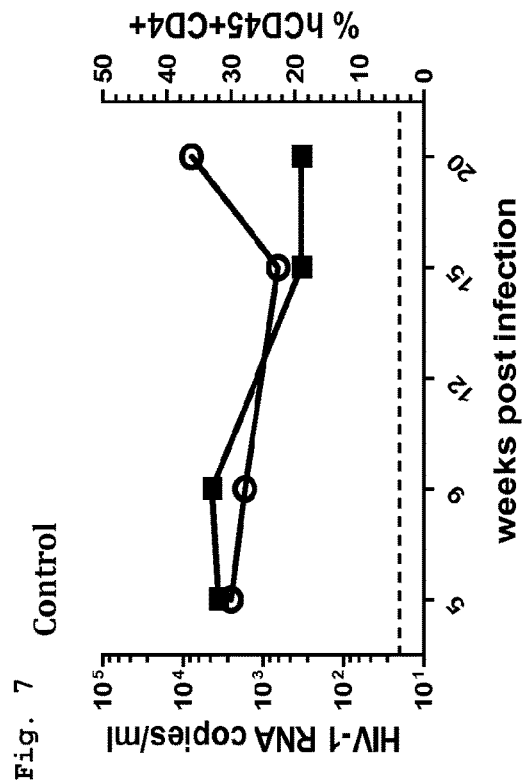
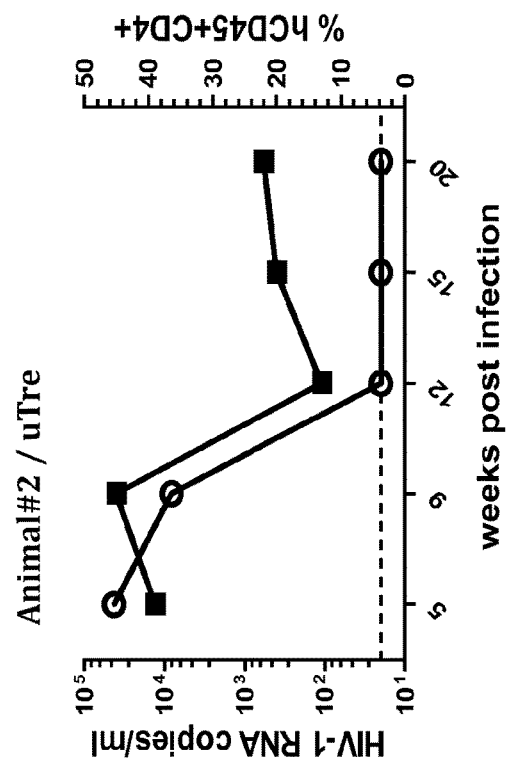
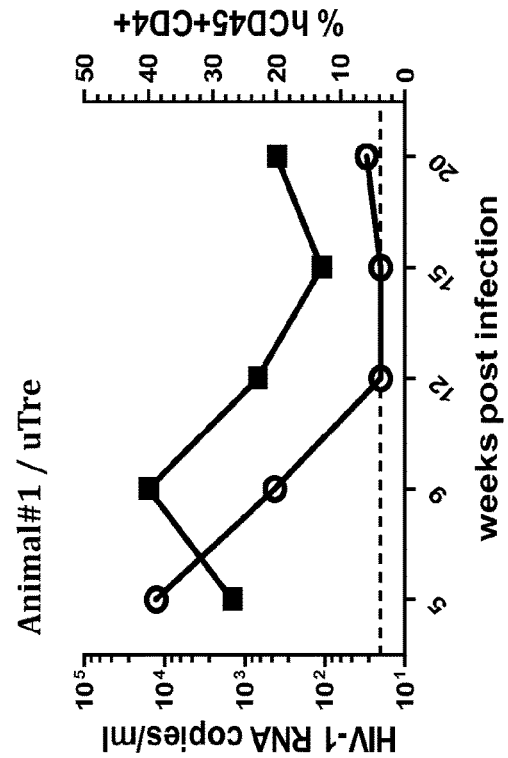
Fig. 7

WELL-TOLERATED AND HIGHLY SPECIFIC TAILORED RECOMBINASE FOR RECOMBINING ASYMMETRIC TARGET SITES IN A PLURALITY OF RETROVIRUS STRAINS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 440098_403USPC_SEQUENCE_LISTING.txt. The text file is 25.5 KB, was created on Feb. 19, 2017, and is being submitted electronically via EFS-Web.

The present invention relates to a method for preparing an expression vector encoding a well-tolerated and highly specific tailored recombinase, which tailored recombinase is capable of recombining asymmetric target sequences within the long terminal repeat (LTR) of proviral DNA of a plurality of retrovirus strains which may be inserted into the genome of a host cell, as well as to the obtained expression vector, cells transfected with these, expressed recombinase and pharmaceutical compositions comprising the expression vector, cells and/or recombinase. Pharmaceutical compositions are useful, e.g., in treatment and/or prevention of retrovirus infection, in particular, HIV infection. In particular, the invention relates to well-tolerated and highly specific tailored recombinases capable of combining asymmetric target sequences in a more than 90% of HIV-1 strains, thereby excising the HIV-1 sequences, and expression vectors encoding them.

Retroviral infections such as for example infections by the human immunodeficiency virus (HIV) are still one of the most important and most widespread human diseases.

One approach to treatment of retrovirus, e.g., HIV, is to target the provirus inserted into the genome of the host cell. Excision of the proviral DNA from the host's genome for example would prevent further HIV replication and differs from current methodologies in that it has the potential to eradicate even dormant virus present in the genome of the host.

One class of proteins that were considered for use in this alternative approach are site-specific recombinases (FLOWERS et al, 1997). Site-specific recombinases mediate a multitude of functions in nature from gene rearrangement to genome segregation, such as for example excision, inversion, or integration of defined DNA units (reviewed in STARK et al, 1992).

One of the simplest and best understood recombinases is the Cre recombinase from bacteriophage P1 that resolves genome dimers into monomers by recombination between two identical, i.e., symmetric, double-stranded DNA sites of a particular sequence (HOESS & ABREMSKI, 1985). The Cre recombinase has found widespread use in mouse genetics (NAGY, 2000). Cre is a 38 kDa protein that was named after its function, as it causes recombination (STERNBERG & HAMILTON, 1981). Prerequisite for this recombination is the alignment of two recombination sites recognized by Cre in antiparallel orientation which are then bound by four identical Cre subunits that join to form a ring in which each subunit contacts two adjacent subunits and one half site of one recombination site (HOESS & ABREMS I, 1985). The recombination site recognized by Cre is a 34-bp double stranded DNA sequence known as loxP (from locus of crossing over (x), P1; STERNBERG & HAMILTON, 1981), which is palindromic with the exception of its eight innermost base pairs (referred to as the spacer), which impart directionality to the site.

Some site-specific recombination systems, including the Cre/loxP-system function without accessory proteins or cofactors and function under a wide variety of cellular conditions. However, since the site-specific recombinases function through specific interactions of the recombinase enzyme subunits with their cognate DNA target sequences, the use of these enzymes is restricted by the requirement that the targeted DNA regions must contain appropriately positioned target sites (LEWANDOSKI, 2001). To date, no wild-type recombinase has been identified that recognizes native retroviral sequences as their DNA target sequences.

Extensive mutational and structural analyses of site-specific recombinases have been carried out in recent years to alter their properties and to achieve a better understanding of the intricate mechanisms of these enzymes (for a review see VAN DUYNE, 2001; and COATES et al, 2005). A lot of studies focused on the Cre recombinase to explore its evolvability. Several studies demonstrated that Cre target specificity could be altered when few nucleotides in its loxP recognition site were changed (BUCHHOLZ & STEWART, 2001; SANTORO & SCHULTZ, 2002; RUFER & SAUER, 2002). Further studies addresses the engineering of mutated loxP target sites containing sequences from the LTR of HIV-1 to develop possible target sites for the use of Cre as antiviral strategy (LEE & PARK, 1998; LEE et al, 2000).

The method of directed evolution is a powerful method to select enzymes with altered specificities (reviewed in Yuan et al., 2005; and JOHANNES & ZHAO, 2006). In the beginning this method was used to isolate improved enzymes on the basis of RNA by selecting RNA molecules with altered substrate sites. The use of PCR-based methods allows the screening of very large libraries and the recovery of successful coding regions from a pool of candidates. In the directed evolution of proteins, by contrast, the screening for and the recovery of improved mutants, which are identified by alterations in the properties of the protein, requires a method for retrieving the nucleic acid sequence encoding the protein. The link between the protein and its coding sequence has often been maintained by compartmentalization. Consequently, library screening in directed protein evolution has been limited to "one-by-one" approaches that maintain the compartments, and the advantages associated with screening pools of candidates have not been available.

This limitation has been overcome by the development of methods that allow the crosslinking of proteins to their respective messenger RNAs (mRNAs) using mRNA-protein fusions and ribosome display. Functional screens for improved protein properties were thus coupled to direct retrieval of corresponding coding molecules, and large pools have been screened in vitro (see for example BUCHHOLZ et al, 1998). A further improvement of directed protein evolution was achieved by the so-called substrate-linked protein evolution (SLiPE; BUCHHOLZ & STEWART, 2001), wherein the substrate of the recombinase was placed on the same DNA molecule as the protein coding region. In this manner, when the recombinase was expressed within a compartment, its action altered the DNA substrate next to its own coding region. Consequently, a library could be screened as a pool by PCR to amplify only candidate coding regions that were next to an altered substrate. This allows the screening of large libraries conveniently for rapid retrieval of successful coding regions. This method was applied for altering the DNA specificity of Cre recombinase and adapting it to a new recognition target site (BUCHHOLZ & STEWART, 2001).

In view of the potential of site-specific recombinases and the need of finding an AIDS therapy eradicating HIV-1 provirus from the genome of a host cell, WO 2008/083931 disclosed generation of a tailored recombinase (TRE) that is capable of recombining asymmetric target sites within the LTR of proviral DNA of a retrovirus inserted into the genome of a host cell, thus excising the provirus from the genome of the host cell. The engineered recombinase disclosed in the examples, Tre, recognizes a specific asymmetric site present in a particular HIV-1 strain. The asymmetric target site has a certain homology to the symmetric loxP site recognized by Cre. WO 2008/083931 appreciated that, due to the high sequence variability of retroviruses, in particular, HIV, for treatment of a patient with a different HIV strain, a different tailored recombinase might have to be adapted, or a collection of recombinases prepared containing tailored recombinases specific for a variety of target sequences.

In contrast, WO 2011/147590 A2 provides a tailored recombinase capable of excising a plurality of retrovirus, e.g., HIV strains. Thus, the generated recombinase can be employed for a plurality of HIV infections, without generation of a new recombinase for every strain. The inventors found that in spite of the high sequence variability of retroviruses, using an innovative approach, it was possible to identify asymmetric target sequences present in a high proportion of the viruses of a particular subtype. Surprisingly, it was possible to identify a target sequence present in 96% of HIV-1 subtype B strains, i.e., the prevalent strains in Europe and America (SEQ ID NO:1). A further target sequence present in a lower percentage of HIV-1 strains was also identified (SEQ ID NO:2). Using Cre (SEQ ID NO: 6 as a basis for molecular directed evolution, they also identified several tailored recombinases capable of recombining said asymmetric target sequences, and provided consensus sequences of these tailored recombinases, e.g., SEQ ID NO:7 or Tre 3.0 (SEQ ID NO:8, capable of recombining SEQ ID NO: 1).

In light of this, the inventors addressed the problem of providing an improved tailored recombinase capable of recombining asymmetric target sequences present in a plurality of HIV-1 strains. The inventors have surprisingly found that tailored recombinases having a sequence differing from the consensus sequences SEQ ID NO: 8, as taught by WO 2011/147590 A2, are also highly active on the asymmetric target sequence SEQ ID NO: 1 present in 96% of all HIV-1 subtype B strains, i.e., the prevalent strains in Europe and America, and have improved characteristics. The tailored recombinases according to the invention preferably comprise the consensus amino acid sequence of SEQ ID NO: 9, more preferably, the more specific consensus sequence of SEQ ID NO: 10 or any of SEQ ID NO: 11-13. The tailored recombinases of the present invention have improved specificity and are therefore better tolerated by humans, in particular, in human T-cells, than the tailored recombinases according to the state of the art. The recombinases are preferably highly specific, as they do not have any detectable residual activity on known target sequences of the recombinase from which they were developed, e.g., on loxP (SEQ ID NO:4), loxH (SEQ ID NO:5) or, also on loxLTR Tre 1.0 (SEQ ID NO:3).

The present invention for the first time provides a method for generating an expression vector encoding a well-tolerated and highly specific tailored recombinase capable of recombining asymmetric target sequences within the LTR of proviral DNA of a plurality of retrovirus strains of one species inserted into the genome of a host cell. Recombinases have been tailored to recognize asymmetric target sites different from their native symmetric target sites, which may be present in a plurality of retrovirus strains, by splitting up the substrate into a number of new subsets with smaller differences from the original target and stepwise tailoring recombinases to recognize these subsets (WO 2008/083931 and WO 2011/147590). A combinatorial approach allows selection of functional molecules recognizing the asymmetric target site within a given sequence. Thus, traversing through substrate intermediates during directed molecular evolution, it has been possible to produce enzymes with remote novel asymmetric target specificities. This approach is also employed by the present invention. The present invention adds to the methods taught by WO 2008/083931 and WO 2011/147590, as it introduces steps of selecting tailored recombinases well tolerated by human cells, in particular, human T cells.

Specifically, the invention provides a method for preparing an expression vector encoding a well-tolerated tailored recombinase, which tailored recombinase is capable of recombining asymmetric target sequences within the LTR of proviral DNA of a plurality of retrovirus strains which may be inserted into the genome of a host cell, comprising steps of identifying in the sequence of the LTR of proviral DNA of a plurality of retrovirus strains sequences with a homology of at least 30% to the left half-site sequence and the right half-site sequence of at least one known recombinase target site, wherein the homologous sequences are separated by a spacer of 5-12 nucleotides, and wherein the asymmetric target sequence is found in a plurality of retrovirus strains; and generating, through repeated steps of i) molecular directed evolution on at least one recombinase recognizing the known homologous target site using as substrate modified target sequences based on the sequence of the asymmetric target sequence, but modified to contain only a limited number of variations from the known target sequence; wherein, in each round, the target sequence may vary from the target sequence on which the recombinase is known to act in one, two or three nucleotides; and ii) shuffling the recombinase libraries to obtain recombinase libraries able to recombine target sequences more homologous to the asymmetric target sequence; until at least one recombinase is obtained that is active on the asymmetric target sequence within the LTR of the retrovirus DNA;

repeated steps of negatively selecting against recombination of the known target site by molecular directed evolution and shuffling of the libraries;

selecting said tailored recombinase or recombinases by expressing the library in human cells, in particular, human T cells, and culturing said human cells expressing the tailored recombinase(s) for at least 1 week, preferably, at least 2 weeks, and isolating the nucleic acid(s) of the recombinase(s) from the cultured cells expressing the selectable marker;

and, optionally, cloning the nucleic acid encoding the recombinase(s) into a suitable expression vector.

The invention in particular provides a method for preparing a nucleic acid or an expression vector encoding a well-tolerated and highly specific tailored recombinase, which tailored recombinase is capable of recombining asymmetric target sequences within the LTR of proviral DNA of a plurality of retrovirus strains, comprising the steps of (a) identifying sequences with a homology of at least 30% to the left half-site sequence and the right half-site sequence of at least one known recombinase target site in the sequence of the LTR of proviral DNA of a plurality of retrovirus strains, wherein the homologous sequences are separated by a spacer of 5-12 nucleotides, and wherein the asymmetric target sequence is found in a plurality of retrovirus strains;

(b) identifying two sequences, wherein the first sequence corresponds to the sequence of the asymmetric target sequence of step (a) homologous to the left half-site of said known target site and is referred to as "half-site sequence 1", and wherein the second sequence corresponds to the sequence of the asymmetric target sequence of step (a) homologous to the right half-site and is referred to as "half-site sequence 2";

(c) determining the nucleotides within the sequences of step (b) deviating from the corresponding homologous left half-site and right half-site sequences of the at least one known homologous target site of step (a);

(d) generating a first subset of two target nucleic acids comprising target sequences, wherein the first target sequence is designated subsite 1 and comprises, adjacent to each other and in 5' to 3' order, half-site sequence 1 of step (b), the spacer sequence of the asymmetric target sequence and an inverted repeat of half-site sequence 1, and wherein the second target sequence is designated subsite 2 and comprises, adjacent to each other and in 5' to 3' order, an inverted repeat of half-site sequence 2, the spacer sequence of the asymmetric target sequence and half-site sequence 2 of step (b);

(e) generating a second subset of target nucleic acids comprising modified target sequences on the basis of the target sequences in the first subset of step (d), wherein, in sequences based on subsite 1, in the left half-site sequence, a portion of the nucleotides deviating from the corresponding homologous half-site sequence of the at least one known target-site of step (a) is replaced by the native nucleotides found in said known target-site, until said half-site sequence contains one, two or three nucleotides deviating from said known target site, wherein the right half-site of said modified target sequence is formed by an inverted repeat of said modified left half-site sequence, which is separated from said modified left half-site sequence by the spacer sequence of the asymmetric target sequence, and wherein, in sequences based on subsite 2, in the right half-site sequence, a portion of the nucleotides deviating from the corresponding homologous half-site sequence of the at least one known target-site of step (a) is replaced by the native nucleotides found in said known target-site, until said half-site sequence contains one, two or three nucleotides deviating from said known target site, wherein the left half-site of said modified target sequence is formed by an inverted repeat of said modified right half-site sequence, which is separated from said modified right half-site sequence by the spacer sequence of the asymmetric target sequence, such that in all modified half-site sequences originating from one target sequence of the first subset of step (d) taken together, all deviating nucleotides can be found, whereas none of said modified half-site sequences alone comprises all deviating nucleotides, (f) separately applying molecular directed evolution on at least one recombinase recognizing a known homologous target site according to step (a) using each nucleic acid of the second subset obtained in step (e) as a substrate;

(g) shuffling the recombinase libraries evolved in step (f), wherein all recombinase libraries evolved on sequences based on subsite 1 are combined and shuffled, and wherein all recombinase libraries evolved on sequences based on subsite 2 are combined and shuffled;

(h) applying molecular directed evolution, preferably, substrate-linked protein evolution, on the shuffled libraries obtained in step (g) using each nucleic acid of the subset according to step (d) as a substrate;

(i) shuffling the recombinase libraries evolved in step (h);

(j) applying molecular directed evolution, preferably, substrate-linked protein evolution, on the shuffled library obtained in step (g) using a nucleic acid comprising the asymmetric target sequence of step (a) as a substrate, until at least one recombinase is obtained that is active on the asymmetric target sequence within the LTR of the retrovirus DNA of step (a);

(k) isolating the nucleic acid encoding the least one recombinase obtained in step (j) from the library and cloning it into an evolution vector which allows for negative selection of tailored recombinases recombining the known target site according to step (a), thereby obtaining a library;

(l) applying molecular directed evolution, preferably, substrate linked protein evolution, on the library obtained in step (k);

(m) shuffling the libraries obtained in step (l);

(n) isolating the nucleic acid encoding the at least one tailored recombinase obtained in step (m) and cloning it into a vector for expression of the encoded recombinase and a selectable marker in a human cell, thereby obtaining a vector library, (o) transforming human cells, preferably, human T cells, with said vector library obtained in step (n);

(p) culturing the cells expressing said selectable marker for at least 1 week, and selecting for high expression of the selectable marker;

(q) isolating the nucleic acid(s) encoding the recombinase from the cells expressing said selectable marker obtained in step (p);

(r) selecting for a nucleic acid encoding a recombinase capable of recombining the asymmetric target sequence of step (a);

(s) isolating the nucleic acid encoding the least one recombinase obtained in step (f) from the library; and, (t) optionally, cloning the nucleic acid obtained in step (s) into a suitable expression vector.

In step (a) of the method of the present invention, the sequence of the LTR of the proviral DNA may be determined, such as for example by DNA sequencing using chain-terminating inhibitors (SANGER et al, 1977). However, if the sequence of the LTR of the retroviral DNA inserted into the genome of the host has already been determined, the sequence can be determined by reference to a database. On the basis of the sequence information computer-based analysis of the sequence information is performed to identify therein sequences with homology of at least 30% to the left half-site and the right half-site sequences of known target sites, respectively, of known recombinases that are separated by a suitable spacer of 5-12 nucleotides, wherein the asymmetric target sequence is found in a plurality of retrovirus strains. Preferably, the homology to the left half-site and the right half-site sequences of known target sites is at least 40% or at least 50%. Preferably, these retrovirus strains are of one species or one subtype thereof. Preferably, a plurality of strains comprises more than 10 strains, more preferably, more than 100 strains, more than 130 strains, more than 200 strains or more than 300 strains, e.g., HIV strains. The strains may be from one subtype of the virus, e.g., HIV-1, HIV-1 subtype A, B and C, preferably, HIV-1 subtype B. Thus, the obtained recombinase or expression vector encoding the same can be used for treatment of infection with a plurality of strains, e.g., more than 50%, more than 70%, more than 80%, more than 90% or all known strains of a retrovirus or subtype thereof.

The term "recombinase" as used herein refers to a protein involved in recombination. As such recombinases recognize and bind two specific DNA sequences termed "recombination sites" or "target sites" and mediate recombination between these two target sites. Accordingly, the term "recombinase" is meant to refer to any protein component of any recombinant system that mediates DNA rearrangements in a specific DNA locus. Naturally occurring recombinases recognize symmetric target sites consisting of two identical sequences termed "half-site" of approximately 9-20 bp forming an inverted repeat, wherein the half-site sequences are separated by a spacer sequence of 5-12 bp.

Recombinases from the tyrosine integrase family are characterized by having a tyrosine as the active site nucleophile that is utilized for DNA cleavage, whereas recombinases from the serine integrase family use a serine instead of a tyrosine.

In one embodiment of the present invention, the at least one known recombinase whose target sequence is used in step (a) and upon which molecular directed evolution is applied in steps (h) and (j) belongs to the family of serine integrases. Preferred recombinases belonging to the family of serine integrases are selected from the group consisting of phiC31 integrase (COMBES et al., 2002), any component of Gin or Hin recombination systems, Tn3 resolvase (KRASNOW & COZZARELLI, 1983) or any other member of the large serine recombinases, Rag1, Rag2 or any other component of the VDJ recombination system or variants thereof.

In another embodiment, said recombinase belongs to the family of tyrosine integrases. Preferred recombinases belonging to the family of tyrosine integrases are selected from the group consisting of Cre from Phage P1 (ABREMSKI et al, 1983, 1984), FLP recombinase from yeast (VOLERT & BROACH, 1986), Dre from phage D6 (SAUER & MCDERMOTT, 2004), R recombinase from *Zygosaccharomyces rouxii* plasmid pSR1, A recombinase from *Kluveromyces drosophdarium* plasmid pKD1, A recombinase from the *Kluveromyces waltii* plasmid pKW1, Tnp1 from the *Bacillus* transposon Tn4430, any component of the λ Int recombination system or variants thereof. Preferably, said recombinase is Cre recombinase or a variant thereof.

The term variant in this context refers to proteins which are derived from the above proteins by deletion, substitution and/or addition of amino acids and which retain some or all of the function inherent in the protein from which they are derived.

In a preferred embodiment, the known recombinase is a chimeric recombinase obtained by for example "family shuffling" as described by CRAMERI et al. (1998). Prerequisite for the employment of family shuffling is a significant homology between the recombinases used for generating the chimeric recombinases. An example for a chimeric recombinase that can be used in the present invention is a chimeric recombinase consisting of sequences of recombinase Cre and of recombinase Dre, respectively.

In a more preferred embodiment the recombinase is the Cre recombinase recognizing a symmetric target site of 34 bp known as loxP. The loxP site (and also other recombination sites of wild-type recombinases) is palindromic with two 13 bp repeats separated by the eight innermost base pairs, which represent the so-called spacer, which imparts directionality to the site. Recombination takes place by cleavage within the spacer sequence. Depending on the relative location and orientation of the two participating loxP sites, Cre catalyzes DNA integration, excision or rearrangement (HOES S & ABREMSKI, 1985).

One useful recombinase is Zre isolated from *Salmonella enterica*, or variants, fragments and homologues thereof, e.g., having a homology of at least about 70%, at least about 80%, at least about 90% or at least about 95% to the wildtype sequence, and having recombinase function. Zre recombinases recombine DNA at zox sites. They can be used for starting the method of the invention either alone or in the context of a library.

In the most preferred embodiment, a recombinase library is used as a starting point for molecular evolution, e.g., a recombinase library comprising different wildtype and/or adapted/shuffled recombinases, e.g., as described, e.g., in Example 2 of WO 2011/147590 A2. Such a library is preferably used as a starting point used for generation of the tailored recombinases able to recognize SEQ ID NO:1, or alternatively, SEQ ID NO:2.

The tailored recombinase obtained by the method of the invention is capable of recombining asymmetric target sequences within the LTR of proviral DNA of a plurality of retrovirus strains. The proviral DNA targeted by the recombinase may be inserted into the genome of a host cell. Alternatively, the tailored recombinase of the invention may recombine asymmetric target sequences within the LTR of proviral DNA of a plurality of retrovirus strains which are not (yet) integrated into the genome of a host cell, i.e. which is present as a non-integrated pre-integration complex (PIC). Thus, HIV which has not yet integrated into the genome of the host cell as well as HIV which already has integrated can be inactivated by the tailored recombinase of the invention.

It is to be noted that in the present invention and also in the art the terms "target sequence", "target site" and "recombination site" are used interchangeably.

Contrary to the naturally occurring recombinases recognizing symmetric target site, the method of the present invention provides tailored recombinases recognizing target sites which do not consist of palindromic sequences separated by a spacer. Instead, in the asymmetric target sites the sequences do not form a symmetric inverted repeat. Accordingly, a tailored recombinase able to recognize an asymmetrical target site should recognize and recombine target sites consisting of half-sites of varying sequence.

Within an asymmetric target site, the sequences referred to as "left half-site" and "right half-site", respectively, are defined by their homology to the left and right half-site of a known target site. The sequence located between the sequences homologous to the left and right half-site of a known target site is referred to as spacer.

However, if sequences are found in the LTR that have only homology to either the left or the right half-site sequence of a known target site, these sequences could nevertheless be used in the practice of the present invention. The size of the target site belonging to the recombinase, whose native target sequence shows homology to sequences within the LTR, is known to the skilled person. For example, if homology is found within the LTR sequence to a target sequence recognized by the Cre recombinase, an asymmetric target site to be recognized by Cre recombinase should consist of 34 nucleotides with two half-site sequences of 13 nucleotides each separated by a spacer of 8 nucleotides. Accordingly, the homologous sequence within the LTR is defined as either the left or the right half-site or the spacer of the asymmetric target site depending on the homology to the sequence of the known target site. Thus, sequences with homology to the left half-site of a known target sequence are defined as left half-site, sequences with homology to the right half-site of a known target sequence are defined as right half-site. Starting from this definition, the other parts of the asymmetric target sites are defined under consideration of the structure of the known target site. Thus, having defined for example a right half-site sequence within the LTR over homology to a loxP site (recognized by Cre recombinase), the other sequences corresponding to the spacer and the left half-site of the asymmetric target sequence can easily be defined. The spacer sequence is for example defined by counting 8 nucleotides upstream of the 5' end of the sequence defined as right half-site sequence, whereas the left half-site sequence is similarly defined by counting 13 nucleotides upstream of the 5' end of the previously defined spacer sequence.

Homology in this context as well as in the whole application means sequence identity. A preferred comparison for homology purposes is to compare at least two sequences using standard techniques known in the art, including, but not limited to, the local homology algorithm of SMITH & WATERMAN (1981), the homology alignment algorithm of NEEDLEMAN & WUNSCH (1970), or the search for similarity method of PEARSON & LIPMAN (1988). For the purposes of the present application sequence homology is preferably determined using the ClustalW computer program available from the European Bioinformatics Institute (EBI), unless otherwise stated.

In view of the requirement of two identical target sites that must be present in the genome of the provirus to allow the recombinase to excise the sequence between these two target sites, sequences of the proviral DNA are scanned in step (a) of the method of the present invention that are present at least twice in the genome. Such sequences are for example the LTR sequences of the proviral DNA. Accordingly, the sequence of the LTR is preferably scanned, since the 5'-LTR and the 3'-LTR of the proviral DNA are identical. An asymmetrical target site present in the 5'-LTR is also present in the 3'-LTR and thus allows for excision of the proviral DNA located between the LTRs.

Out of the sequences identified within the LTR sequence having sufficient homology to known target sites, sequences are preferably chosen that have the highest homology to the sequence of the target site of known recombinases. However, it is also possible to select sequences other than those having the highest homology, e.g., those that are present in the highest number of retrovirus strains, or in the retrovirus strains of interest, e.g., if a patient is infected with a particular strain.

It is to be noted that the potential of the method of the present invention even allows tailoring recombinases that recognize asymmetric target sites with less than 30% homology to known target sites, e.g., at least 11%) or at least 20% homology. However, to ensure the presence of residual recombination activity for the respective asymmetric target site or subsites therefor, it is preferably scanned for sequences having a homology of at least 30% to the left half-site and the right half-site sequences of known target sites of known recombinases. In further preferred embodiments asymmetric target sequences having a homology of at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80%, more preferably 85%), particularly preferably 90% and most preferably 95% to the left half-site and the right half-site sequences of known target sites of known recombinases are selected.

In one embodiment of the present invention, the sequence selected within the LTR has homology to the symmetric loxP target sites recognized by the site specific recombinase Cre.

In one preferred embodiment, a recombinase library is used as a starting point for molecular evolution, e.g., a recombinase library comprising different wild type and/or adapted/shuffled recombinases such as the library described in Example 2 of WO 2011/147590 A2. An exemplary library comprises Cre and recombinases derived therefrom. It may also comprise Tre, Dre, recombinases from *Salmonella* and *Shewanella* and/or recombinases derived therefrom. The library may comprise, e.g., Cre, Dre, Dre "Cre-ed", *Shewanella* recombinase (Shew), Shew "Cre-ed", and/or Zre, as disclosed in WO 2011/147590 A2. Tre is a tailored recombinase as disclosed by WO 2008/083931, which is also further referred to as Tre 1.0.

In one embodiment, all recombinases in the library recognize a target sequence with the same length of spacer. The total length of the half-site sequences 1 and 2 including spacer preferably is 34 nucleotides.

If the at least one recombinase is a recombinase library, the homology is homology to the pool of known recombinase target sites (i.e., homology in a given position to at least one of a target sequences is defined as homology). Consequently, in step (c), only those nucleotides which do not correspond to a nucleotide in at least one of the known target sequences are defined as deviating nucleotides. In the case of a recombinase library, a "native nucleotide" in step (e) can be a nucleotide present in that position in any of the known target sequences, preferably, it is a nucleotide present in that position in several or most of the known target sequences.

To identify target sequences present in a plurality of retrovirus strains, the known recognition sites of recombinases, which have been described in literature, can be used as a query for a search for conserved asymmetric target sequences against a genomic stretch. Given the repetitive nature of regions, the use of standard sequence similarity search tools however is precluded. Sarkar et al., 2007, used BLAST (ALTSCHUL et al., 1997) to find a lox-like binding site across HIV strains. The BLAST search for the lox-like site when performed across HIV-1 LTR sequences resulted in the discovery of only one site present in a single strain. BLAST does not perform well with such short redundant sequences, and alternative programs such as HMMER (EDDY et al, 1998), RepeatMasker or the palindrome program from the Emboss suite of packages also proved not suitable. With a specific program using an algorithm based on a position weight matrix for the flanking regions based on a known recognition site of a recombinase, and using binary operations on the sequences after they were transformed into bit strings, asymmetric target sequences found in a plurality of retrovirus strains were identified WO 2011/147590 A2.

For HIV-1, suitable asymmetric target sequences were determined, having sequence set forth as SEQ ID NO:1 or SEQ ID NO:2 below. This renders it possible to generate recombinases, which are practically useful as therapeutic agents against retroviral genomes in a significant number of patients, as these recombinases target recognition sites present across as many strains of the retrovirus as possible.

The left half-site and right half site sequences of SEQ ID NO: 1 and 2 are underlined and the spacer is printed in bold:

SEQ ID NO: 1
AACCCACTGCTTAAGCCTCAATAAAGCTTGCCTT

SEQ ID NO: 2
CTGGGCGGGACTGGGGAGTGGCGAGCCCTCAGAT

SEQ ID NO: 1 is present in 96% of the HIV-1 subtype B strains searched (1024/1067), in 92% of the HIV-1 subtype C strains searched (624/679), and in 82% of the HIV-1 subtype A strains searched (71/87). SEQ ID NO: 2 is identical in a lower percentage of subtype B and C strains.

SEQ ID NO: 1 has 54% homology to a pool of known recombinase target sites, and SEQ ID NO:2 has 42% homology to the pool of these sequences (with regard to the left and right half-sites, respectively). Homology to individual known target sites is lower, e.g., at least 30% for SEQ ID NO: 1 and at least 11% for SEQ ID NO:2. In particular in the case of low individual homology to known target sites, it can be advantageous to use a library of recombinases as the starting material, e.g., for generating a tailored recombinase capable of recombining SEQ ID NO: 1 or SEQ ID NO:2, a library comprising Cre, Fre, Dre, Zre and Tre.

In step (b) of the method of the invention, the sequence of the asymmetric target site within the LTR of the proviruses which is homologous to the left half-site of the known target site is defined as "half-site sequence 1". The sequence of the asymmetric target site within the LTR of the proviruses which is homologous to the right half-site of the known target site is defined as half-site sequence 2. The sequence between the sequences representing the left and the right half-site is referred to as the spacer.

In step (c), the nucleotides within "half-site sequence 1" and "half-site sequence 2", respectively, of the sequences of step (b) deviating from the sequences of the corresponding homologous left half-site and right half-site sequences of the known target are determined by sequence alignment and sequence comparison. In this context, the sequence of "half-site sequence 1" is compared to the corresponding native half-site, which is preferably the left half-site sequence, whereas the sequence of "half-site sequence 2" is compared to other half-site forming the palindromic native target site, which is preferably the right half-site sequence.

FIG. 1 of WO 2011/147590 A2 shows the result of this comparison for SEQ ID NO: 1 and 2, compared to a library of recombinases. Deviating nucleotides are shown before a dark background.

This comparison must not necessarily performed after step (b) and prior to step (d) of the method of the invention, but can also be performed in a different phase of the method after step (a) and prior to step (e).

In step (d), a first subset of two target nucleic acids comprising target sequences is generated, wherein the first target sequence is designated subsite 1 and comprises, adjacent to each other and in 5' to 3' order, half-site sequence 1 of step (b), the spacer sequence of the asymmetric target sequence and an inverted repeat of half-site sequence 1, and wherein the second target sequence is designated subsite 2 and comprises, adjacent to each other and in 5' to 3' order, an inverted repeat of half-site sequence 2, the spacer sequence of the asymmetric target sequence and half-site sequence 2 of step (b). The target sequences of the first subset are palindromic oligonucleotide sequences having the structure of a symmetric target site. These artificial symmetric target sites are synthesized on the basis of the half-site sequences of step (b) by complementing the missing half-site sequence in each oligonucleotide sequence as inverted repeat, wherein the sequence of "half-site sequence 1" and "half-site sequence 2", respectively, is used to complement the second half-site sequence at the opposite end of the spacer sequence. Accordingly, the first target sequence in the first subset (referred to as "subsite 1") comprises an inverted repeat consisting of the "half-site sequence 1" and the inversely repeated "half-site sequence" separated by the spacer sequence, whereas the second target sequence in the first subset (referred to as "subsite 2") comprises an inverted repeat consisting of the inversely repeated "half-site sequence 2'" and "half-site sequence 2" separated by the spacer sequence. In "subsite 1" the sequence are arranged as follows: 5'-"half-site sequence 1"-spacer-"inverted repeat of half-site sequence 1"-3', in "subsite 2" the sequence are arranged as follows: 5 '-"inverted repeat of half-site sequence 2'"-spacer-"half-site sequence 2"-3'.

The spacer sequences within each two synthetic target sequences of the first subset are preferably identical and correspond to the sequence of the LTR representing or defined as the spacer sequence of the asymmetric target site. However, in a further embodiment, the spacer sequences may comprise one or two sequence deviations originating from nucleotide substitutions.

Generally, this step represents a first split up of the sequences of the asymmetric target site selected for tailoring a specific recombinase (see FIG. 1 of WO 2008/083931, which is fully incorporated herein by reference, and FIG. 2 of WO 2011/147590 A2, which is also fully incorporated herein by reference). Sequences are generated in this step harbouring symmetric target sites derived from the half-sites of the asymmetric target site selected for tailoring a specific recombinase. As a consequence, each mutation (i.e. difference to the target site(s) recognized by the original (wild-type) recombinase(s)) present in one half-site of said asymmetric target site has now been spread up between the symmetric target sequences in the first subset.

In step (e) of the method of the invention, a second subset of target nucleic acids comprising modified target sequences is generated on the basis of the target sequences in the first subset of step (d). In sequences based on subsite 1, in the left half-site sequence, a portion of the nucleotides deviating from the corresponding homologous half-site sequence of the at least one known target-site of step (a) is replaced by the native nucleotides found in said known target-site, until said half-site sequence contains one, two or three (preferably, two) nucleotides deviating from said known target site, wherein the right half-site of said modified target sequence is formed by an inverted repeat of said modified left half-site sequence, which is separated from said modified left half-site sequence by the spacer sequence of the asymmetric target sequence.

In sequences based on subsite 2, in the right half-site sequence, a portion of the nucleotides deviating from the corresponding homologous half-site sequence of the at least one known target-site of step (a) is replaced by the native nucleotides found in said known target-site, until said half-site sequence contains one, two or three (preferably, two) nucleotides deviating from said known target site, wherein the left half-site of said modified target sequence is formed by an inverted repeat of said modified right half-site sequence, which is separated from said modified right half-site sequence by the spacer sequence of the asymmetric target sequence.

For example, if one subsite comprises six deviating nucleotides, such as both subsites based on SEQ ID NO:1 or subsite 2 of SEQ ID NO:2 with regard to the library of recombinases shown in FIG. 1 of WO 2011/147590 A2, three modified target sequences can be generated based on the subsite, which each contain two (different) deviating nucleotides in the left half-site (if based on subsite 1) or right half-site (if based on subsite 2). Consequently, in each modified target sequence, the sequence of the respective subsite is modified to correspond to the sequence of the known target sequence (or at least one known target sequence) in four nucleotides (FIG. 2 of WO 2011/147590 A2). Of course, it is also possible to generate six modified target sequences each containing one of the deviating nucleotides, or two target sequences each containing three of the deviating nucleotides.

In another example, if one subsite comprises nine deviating nucleotides, such as subsite 1 of SEQ ID NO:2 with regard to the library of recombinases shown in FIG. 1 of WO 2011/147590 A2, three modified target sequences can be generated based on the subsite, which each contain three (different) deviating nucleotides in the half-site.

As a consequence, in all modified half-site sequences originating from one target sequence of the first subset of step (d) taken together, all deviating nucleotides can be found, whereas none of said modified half-site sequences alone comprises all deviating nucleotides.

Again, an inverted repeat is generated on the basis of the modified half-site sequence, such that the spacer sequence separates both sequences forming the inverted repeat (see FIG. 2 of WO 2011/147590 A2). The spacer sequences within each modified target sequences of a new subset being derived from a target sequence of a higher subset are preferably identical and correspond to the sequence of the LTR representing or defined as the spacer sequence of the asymmetric target site. However, in a further embodiment the spacer sequences may comprise one or two sequence deviations originating from nucleotide substitutions. Using this approach, the number of mutations (i.e. differences to the target site recognized by the wild-type recombinase) in the target sequences representing each subset is smaller than in the starting asymmetric target sequence, but all mutations are still represented in one of the target sequences (see FIG. 1 of WO 2008/083931, FIG. 2 of WO 2011/147590 A2).

The term "deviating nucleotide" as used herein refers to a nucleotide within the asymmetric target sequence identified or defined within the LTR or within a target sequence of a subset generated according to the present invention that deviates (i.e. is different) from the nucleotide present at the same position in the corresponding homologous sequence of the known homologous symmetric target sequence of a known recombinase chosen in step (a) of the method of the present invention. In this context, the terms "deviating nucleotides" and "mutations" are used interchangeably.

WO 2008/083931 teaches that recombinases can be tailored using molecular directed evolution using target sequences as a substrate, if the target sequence used as a substrate differs in not more than 3 nucleotides from the native target sequence. Thus, the generation of subsets of different orders described above serves to reduce the number of deviating nucleotides per target sequence to 3 or less (see FIG. 1 of WO 2008/083931). The stepwise reduction of the number of deviating nucleotides finally yields a number of subsets of target sequences of different orders with decreasing numbers of deviating nucleotides until a final subset is created that can be used as a substrate for molecular directed evolution. While creating the different subsets and thereby reducing the number of deviating nucleotides, the differences to the target site recognized by the wild-type recombinase are spread between several target sequences that do not comprise more than 3 of these deviating nucleotides each, while the target sequences of the final order as a whole still represent all deviating nucleotides.

Optionally, in the method of the invention, further subsets of target sequences can be generated starting from the target sequences of the second subset by stepwise repeating the process of step (e), i.e. splitting up the target sequences into the respective half-site sequences and generating new palindromic structures on the basis of these half-site sequences after altering the sequence of the half-site derived from a target sequence of the second subset, each time generating a new subset of target sequences, wherein the half-site sequences used for generating the inverted repeats contain less nucleotides deviating from the corresponding homologous half-site sequence of the at least one known target site. These additional target sequences can be used for additional steps of directed molecular evolution and shuffling of recombinase libraries. Of course, such an additional step can also only be performed for some of the sequences, e.g., for sequences wherein recombinases with a low efficiency of recombination are obtained. If additional subsets are generated and recombinases evolved on these, the evolved library of recombinases is used in step (f) of the method of the invention.

Starting from the second subset of target sequences obtained in step (e), a third subset may be generated, followed by a fourth, fifth, sixth etc. subset if necessary. However, the generation of the third subset is generally only necessary, if the target sequences of the second subset still contain more than three deviating nucleotides. The same applies to the generation of the next subsets, which are only necessary, if the target sequences of the prior subset still contain more than three deviating nucleotides. It should be noted that in one embodiment, subsets of target sequences will be generated until the target sequences of the final subset only comprise one deviating nucleotide. Accordingly, depending on the number of deviating nucleotides in each half-site sequence, the number of subsets generated for each half-site sequence of the asymmetric target site may differ. It may for example be necessary to generate only two subsets for the left half-site sequence, whereas three or four subsets must be generated for the right half-site in order spread the deviating nucleotides between several target sequences such that a single target sequence does not comprise more than 3 of these deviating nucleotides.

The principle of generating further subsets of the target sequences for reducing the number of deviating nucleotides to numbers below three is illustrated in FIG. 1 of WO 2008/083931, and FIG. 2 of WO 2011/147590 A2 provides specific examples of modified target sequences.

In step (f), a method of molecular directed evolution is applied on the at least one recombinase recognizing a known homologous target site of step (a), using a target sequence of the final or second subset obtained in step (e) containing one, two or three nucleotides deviating from the corresponding homologous half-site sequence of said known homologous target site as a substrate.

The term "final subset" as used herein refers to the last subset generated in step (e), i.e., if no additional subsets are generate, on the second subset. Depending on the number of deviating nucleotides in the asymmetric target site and number of subsets that had to be generated to reduce the number of deviating nucleotide per target sequence below 3, the "final subset" may correspond to any subset, for example the second, third, fourth or a later subset, and may be different for the half-site sequences of the asymmetric target sequence within the LTR. If recombinases have previously been evolved on additional subsets of modified target sequences having less nucleotides deviating from the corresponding homologous half-site sequence of said known homologous target site, the recombinase obtained in that step is used.

Of course, it is possible to start the process of the invention with a specific recombinase for a specific modified target sequence, and with another recombinase (or a library) for another specific modified target sequence. Methods of molecular directed evolution, also referred to as laboratory evolution or in vitro-evolution, are known in the art (for a review see YUAN et al, 2005 and references therein; JOHANNES & ZHAO, 2006).

In a first step of molecular directed evolution, libraries of randomly mutated recombinase sequences are generated by methods known in the art, e.g. by using error prone PCR and DNA shuffling (reviewed in e.g. YUAN et al., 2005), or the methods disclosed in the International Patent application WO 2002/44409. The plasmids of each library comprising the mutated recombinase also contain one of the target sequences of the final subset obtained in step (f). After transfection of the generated plasmid library into appropriate cells, expression of the recombinase is enabled and the molecular directed evolution is carried out as known by the person skilled in the art.

In a preferred embodiment, the molecular directed evolution employed in step (f) of the method of the present invention is substrate-linked protein evolution (SLiPE; Buchholz & Stewart, 2001; International Patent application WO 02/44409). The substrate-linked protein evolution may be carried out as described in detail in the examples of WO 2008/083931 or WO 2011/147590 A2. Briefly, the target sequences obtained in step (e) are cloned into a plasmid (the so-called evolution vector) together with a randomly mutated coding sequence for the recombinase. The random mutation is carried out by error-prone PCR (see BUCHHOLZ & STEWART, 2001). The generated plasmid library is then transfected into E. coli cells to allow expression of the recombinase. By using an inducible promoter to drive the expression of the recombinase, it is possible to adjust the expression levels. After overnight incubation, plasmid DNA is isolated from the cells and is digested with NdeI to cut the plasmids that were not recombined and only recombined plasmids are subsequently amplified with primers. The PCR product of the recombined form of the plasmid produces a 1.7 Kb band. The PCR product is digested with BsrGI and XbaI and subcloned back into similarly digested evolution vector for the next evolution cycle.

In step (g), the recombinase libraries evolved in step (f) are combined and shuffled. The technology of DNA shuffling is known in the art (for a reviewed see MINSHULL & STEMMER, 1999; STEMMER, 1994). The recombinase libraries evolved on modified target sequences based on subsite 1 are combined and shuffled, and, separately, the recombinase libraries evolved on modified target sequences based on subsite 2 are combined and shuffled. The combined and shuffled libraries are then cloned into a new generation of vectors comprising the target sequences of the next higher subset, i.e., if two subsets are generated, the subset generated in step (d). For example, the vector for the library evolved on the sequences based on subsite 1 comprises the sequence of subsite 1 as a target sequence, and the vector for the library evolved on the sequences based on subsite 2 comprises the sequence of subsite 2 as a target sequence.

In step (h), the method of molecular directed evolution is applied on the shuffled libraries obtained in step (g) using the target sequence of the next higher subset, which, as discussed may be the subset according to step (d). In this step, the same method of molecular directed evolution as those applied before in step (f) can be used, but it is also possible to use a different method of molecular directed evolution in this step of the method of the present invention. Examples of different methods of molecular directed evolution were described for example by YUAN et al. (2005). Preferably, the method of substrate-linked protein evolution is also applied on the combined and shuffled libraries.

This step yields recombinases recognizing and recombining target sequences harboring the combination (and thus increasing numbers) of mutations from the different target sequences of the lower subset. The combination of mutations from the different libraries of a lower subset of target sequences results in synergistic effects and leads to the generation of recombinases, which now recombine target sequences of a higher subset, demonstrating that an evolution strategy traversing through intermediates can be used to achieve a desired activity.

In step (i), the steps (g), i.e. combining and shuffling of recombinase libraries, and (j), i.e. the application of molecular directed evolution on the combined and shuffled libraries, are repeated until at least one recombinase is achieved that is active on the asymmetric target sequence present in the LTR of the proviral DNA.

In a method wherein the generation of two subsets of target sequences was necessary to generate target sequences with only one, two or three nucleotide deviations, the recombinase libraries evolved for example for the second subset of target sequences are combined and shuffled and molecular directed evolution is applied on this shuffled library using the target sequences of the first subset. In the next step, the asymmetric target sequence of step (a) within the LTR of the proviral DNA is used to evolve the recombinase library comprising recombinases recognizing the target sequences of the first subset by molecular directed evolution to obtain at least one recombinase that is active on the asymmetric target sequence within the LTR of the retroviral DNA. In this step, the method of molecular directed evolution preferably is the method of substrate-linked protein evolution.

"At least one recombinase" refers to the fact that the method of the invention might lead to one or more (single) recombinases which are, each for itself, active in recombining the asymmetric target sequence. It is not intended to encompass several different recombinases which only together are capable of recombining the asymmetric target sequence. In fact, the method of the invention would not lead to selection of recombinases which need to be combined with other, different recombinases to recombine an asymmetric target sequence, because only one recombinase per individual cell is expressed.

Method steps (a)-(j) are, in essence, known in the art, in particular, from WO2011/147590. After step (j), the library of tailored recombinases is negatively selected for recombination of the known symmetric target site according to step (a), e.g., for recombination of loxP and/or loxH.

This selection may be effected by at least one cycle of one or more steps comprising targeted molecular evolution and shuffling of the vector library.

To this end, the nucleic acid encoding the at least one tailored recombinase evolved in the previous steps may be isolated from the vectors used therein, and cloned into a suitable evolution vector. Said vector allows for negative selection of tailored recombinases recombining the known target site according to step (a), e.g., for recombination of loxP (SEQ ID NO:4) and/or loxH (SEQ ID NO:5). A library of vectors is thereby obtained. Molecular directed evolution, preferably, substrate linked protein evolution (SLiPE) is then employed, as known to the skilled person and according to the principles described above.

For example, the evolution vector can be constructed so that it comprises both the final asymmetric target sequence (e.g., SEQ ID NO:1) and the known target site (e.g., loxP and/or loxH), each twice to allow for recombination. Recombination at the known target site and following restriction digest lead to a linear product which does not comprise two specific primer sites in an order allowing PCR amplification of a product. If no recombination takes place at all, the vector is linearized by restriction digest, and no amplification by PCR takes place. In contrast, recombination at the final asymmetric target site (e.g., SEQ ID NO:1) cuts out the restriction site, i.e, the vector is not linearized by restriction digest, and the tailored recombinase can be amplified by PCR. PCR, which inherently produces errors, is used to generate variability. Evolution can be carried out in *E. coli*.

The library obtained after one or more, preferably, after about ten cycles of molecular directed evolution, can be shuffled. One or more further cycles of molecular directed evolution and/or shuffling can be carried out.

Optionally, negative selection for recombination of several known target sites, e.g., for recombination of loxP and loxH can be carried out alternately, e.g., one cycle of evolution with negative selection on loxP can be alternated with one cycle of evolution with negative selection on loxH. For example, about 10 to about 30 or about 15-20 cycles of negative selection, combined with about two rounds of DNA shuffling, can be carried out. Between these evolution cycles, the amount of the transcription activator L-arabinose can be varied, e.g., from 100 µg/mL to 1 µg/mL. Preferred vectors and methods are shown in FIG. 2 and the examples.

Specificity of the tailored recombinases on the final asymmetric target sequence and potential residual activity on the known target sequences can be checked for one or more clones after a number of evolution cycles have been carried out.

If specificity is not yet satisfactory, further evolution cycles should be carried out.

As shown in FIG. 3, the negative selection removes residual activity of tailored recombinases such as those taught by WO 2011/147590 A2 (TRE3) on the known target sequences of loxP and loxH. No residual activity of the generated recombinases of the invention on the known target sites, e.g., loxP and/or loxH, is detectable even in the presence of high amounts (50 or 100 µg/ml) of the transcription activator L-arabinose, i.e., in presence of high amounts of recombinase. This shows that the obtained tailored recombinases are highly specific for their target sequence, in this case, for SEQ ID NO:1, as the specific asymmetric target sequence is recombined, but the known symmetric target sequence is not.

This has the advantage that, when the tailored recombinase of the invention is applied for therapy of humans, the risk of cross-reaction with and recombination of human sequences in the host cell is minimal. This is one factor contributing to tolerability of the tailored recombinase in human cells. However, not only short-term consequences of expression of the recombinase are at issue here, but also safety aspects such as possible oncogenic effects of unspecific recombination, even at low efficacy. Elimination of even residual activity of the tailored recombinase thus contributes to safety and reliability of the resulting tailored recombinase in therapeutic settings.

The selection against recombination of the known symmetric target sequences is followed by selection for a tailored recombinase well tolerated in human cells.

In step (n) of the method of the invention, the nucleic acid encoding the at least one tailored recombinase obtained in step (m) is isolated and cloned into a vector for expression of the encoded recombinase and a selectable marker in eukaryotic, preferably, human cells, thereby obtaining a vector library. The nucleic acid may be isolated from the respective plasmid within the library using appropriate restriction enzymes. Methods of restriction endonuclease digestion are known to skilled person. The nucleic acid encoding the recombinase can then be recovered by known methods such as for example gel electrophoresis. It may be cloned into an appropriate expression vector for expression in eukaryotic, e.g., human, cells, as known in the state of the art or described below. For example, a retroviral, e.g., lentiviral vector may be used, e.g., as shown in FIG. 4A. Expression of the encoded tailored recombinase and the selectable marker preferably is constitutive, or it may be induced by suitable agents.

The selectable marker may confer resistance to an antibiotic, or it may be a fluorescent protein such as green fluorescent protein (GFP) or a derivative thereof (e.g., EBFB, ECFP, YFP. Fluorescent proteins such as GFP allow for easy cell sorting dependent on the strength of expression.

In step (l), eukaryotic, preferably, human cells, preferably, human T cells, are transformed with said vector library obtained in step (k). Methods known in the state of the art can be used. The transformed cells are usually human cells, however, if therapy for a non-human patient is intended, it is advisable to test tolerability in cells of that patient's species. The human cells preferably are hematopoietic cells, e.g., preferably, T cells, in particular, CD4+ T cells, but stem cells such as CD34+ stem cells can also be used. Primary cells, e.g., primary T cells, preferably, primary CD4+ T cells, may be used, but a cell line such as Jurkat T cells can also be employed.

In step (p), the cells expressing said selectable marker are cultured for a period of time sufficient to select for TRE recombinases well-tolerated by the human cell. The selection is based on the assumption that expression of the marker and the tailored recombinase are correlated. The cells are selected for expression of the marker, e.g., GFP-positive cells are selected, preferably, cells with strong expression of GFP. As expression of the selectable marker and of the tailored recombinase correlate, these cells will also express the tailored recombinase. Cells expressing a tailored recombinase which is detrimental to their survival or their capability for propagation are therefore eliminated or reduced in quantity. Preferably, the cells expressing the marker are cultured for at least 1 week, at least two weeks, at least 3 weeks or at least 4 weeks. Accordingly, the tailored recombinases expressed in the T cells will be well-tolerated by human cells, e.g., human T cells, i.e., it will not be toxic for said cells, or, preferably, also not otherwise detrimental to survival and propagation of said cells. Preferably, during that period of culture, the cells are selected at least one time, preferably, 2, 3, or 4 times, for high expression of the selectable marker. For example, with a fluorescent protein, selection can be performed by fluorescence-activated cell sorting. With an antibiotics resistance gene, rising amounts of antibiotics can be added to the culture medium.

While expression of wild-type Cre recombinase in human cells has been established for a long time, and, at reasonable expression levels, has been shown to be unproblematic, overexpression of Cre can be toxic (LOONSTRA et al., 2001). The inventors found that a significant number of mutated tailored recombinases according to the present invention were detrimental to human T cells' survival and/or propagation upon strong overexpression. Interestingly, even though it could have been expected that it is the relatively low specificity of the tailored recombinases and residual activity on target sites such as loxP and loxH (a sequence present in the human genome) that leads to low tolerability in human cells, selection for tolerability in human T cells alone without previous selection for high specificity was not sufficient in eliminating residual cross-reactivity on loxP or loxH. Thus, only the combination of both selection steps with the previously known method of the invention leads to a tailored recombinase that is both well tolerated and highly specific.

In step (q), the steps of culture and selection are followed by isolation of the nucleic acid encoding the at least one recombinase from the cells expressing said selectable marker obtained in step (p).

Step (r) is optional, and adds another selection for a nucleic acid encoding a recombinase capable of recombining the asymmetric target sequence of step (a), preferably, for recombination with a high activity. Recombination activity is preferably tested in human cells, in particular, human CD4+ T cells, but it may also be tested in E. coli.

In step (s), the nucleic acid of a recombinase having activity on the asymmetric target sequence of step (a) within the LTR of the retroviral DNA is isolated from the library. The nucleic acid may be isolated from the respective plasmid within the library using appropriate restriction enzymes. Methods of restriction endonuclease digestion are known to skilled person. The nucleic acid encoding the recombinase can then be recovered by known methods such as for example gel electrophoresis.

The nucleic acid may be stored (preferably at temperatures below −80° C.) or may optionally be cloned in step (t) into an expression vector for use in further analysis, in protein expression methods, or for the administration to a subject for treating and/or preventing retrovirus infection, in particular, HIV infection and/or AIDS. Suitable expression vectors are known in the state of the art or disclosed below.

The development of tailored recombinases that specifically target asymmetric sequences such as SEQ ID NO:1 within a plurality of HIV-1 LTRs allows the excision of the respective provirus from its chromosomal integration for the majority of subjects infected with HIV-1. An expression vector encoding such a recombinase, cells transfected with it and/or recombinase protein derived therefrom has medical uses, e.g. in treatment and/or prevention of an HIV-1 infection. Preferred methods of preparing such a tailored recombinase or expression vector encoding it are taught in WO 2011/147590. The present inventors added to the method described in WO 2011/147590 a step of active selection for high specificity, i.e., no detectable cross-reactivity on the known target sequence of step (a) (or on, e.g., loxP and loxH), and for tolerability of the tailored recombinase in human cells, such as human T cells. As described, this significantly improves medical use of the tailored recombinase for excising HIV provirus genomes from human T cells.

The proviral DNA which may be inserted into the genome of a host cell, or which may not yet be inserted, preferably is the DNA of a retrovirus. Retroviruses comprise a large and diverse family of enveloped RNA viruses. The hallmark feature of the family is its replicative strategy which includes as essential steps the reverse transcription of the viral RNA into linear double-stranded DNA and the subsequent integration of this DNA (proviral DNA) into the genome of the host cell. Retroviruses are subdivided into seven groups, defined by evolutionary related-ness. Five of these groups (alpha-, beta-, delta-, epsilon-, and gamma-retrovirus) represent retroviruses with oncogenic potential, and the other two groups are the lentiviruses and the spumaviruses. The human pathogenic human T cell leukemia viruses type I and type II (HTLV-I and HTLV-II) belong to the delta-retrovirus group, while the AIDS viruses human immunodeficiency virus type 1 and type 2 (HIV-1 and HIV-2) belong to the lentivirus group (for a review see the standard textbook "Retroviruses" of COFFIN J M, HUGHES S H, VAR U S H E (Eds.) 1997, Cold Spring Harbor Laboratory Press, New York).

In one embodiment, the proviral DNA which may be inserted into the genome of a host cell is the DNA of a retrovirus selected from the group consisting of Mouse mammary tumour virus (MMTV), Mason Pfizer monkey virus (MPMV), Human T cell leukemia virus Type I (HTLV-I), Human T cell leukemia virus Type II (HTLV-II), Simian T cell leukemia virus Type I (STLV-I), Simian T cell leukemia virus Type II (STLV-II), Bovine leukemia virus (BLV), Feline leukemia virus (FeLV) and Moloney murine leukemia virus (MoMLV).

In another embodiment, the retrovirus is a lentivirus selected from the group consisting of Human immunodeficiency virus Type 1 (HIV-1), Human immunodeficiency virus Type 2 (HIV-2), Simian immunodeficiency virus (SIV), Feline immunodeficiency virus (Fly), Bovine immunodeficiency virus (BIV), Maedi-visna virus (MVV), Equine infectious anemia virus (EIAV) and Caprine arthritis encephalitis virus (CAEV). As stated above, HIV, in particular HIV-1 is preferred.

The asymmetric target sequence identified in step (a) of the method of the present invention is localized in both the 5'-LTR and the 3'-LTR of the HIV provirus. Preferably, said asymmetric target sequence localized in both the 5'-LTR and the 3'-LTR of a HIV provirus has the sequence set forth as SEQ ID NO:1 or SEQ ID NO:2.

In a preferred embodiment, the method of molecular directed evolution applied in the method of the present invention is the method of substrate-linked protein evolution (SLiPE; BUCHHOLZ & STEWART, 2001; see also WO 02/44409).

By carrying out the method of the invention as described herein, the inventors generated several nucleic acids encoding a well-tolerated tailored recombinase, and the tailored recombinases themselves. The invention thus provides a well-tolerated tailored recombinase comprising a sequence according to any of SEQ ID NO:9-13 or consisting thereof, or nucleic acids encoding it.

It was surprisingly found that these tailored recombinases differ from the consensus sequences SEQ ID NO:7 and 8 of tailored recombinases capable of recombining asymmetric target sequences as taught by WO 2011/147590, and from all other previously known recombinases.

In particular, the novel analyzed well-tolerated tailored recombinases capable of recombining the asymmetric target sequence of SEQ ID NO: 1 with high specificity, surprisingly comprise a Q89L mutation.

In one embodiment, the tailored recombinases of the present invention comprise a sequence according to SEQ ID NO:9 (Tre 3.1 consensus sequence 85%). SEQ ID NO:9 represents a consensus sequence, with each mutation (as compared to the Cre amino acid sequence) being present with a probability of 85%. For this determination, 100 individual clones generated by the method of the present invention, were analyzed by Sanger sequencing as well as the whole generated Tre 3.1 library by next-generation sequencing (33,000 reads of unique 200 bp-sequences). Variable amino acids are represented by an X, which can stand for any naturally occurring amino acid (cf. FIG. 1). About a third of the amino acids of SEQ ID NO:9 are highly variable, i.e., these positions need not be conserved in order for the recombinase being both capable of recombining the asymmetric target sequence of SEQ ID NO: 1, and of being well-tolerated by humans. About two thirds of the amino acid positions, on the other hand, seem important for recombining the asymmetric target sequence of SEQ ID NO: 1 with high specificity and/or for being well-tolerated by humans.

In a preferred embodiment, the tailored recombinase of the present invention comprises a sequence according to any of SEQ ID NO:11-13, most preferably, SEQ ID NO:11. These tailored recombinases were selected for their specificity, i.e., while other recombinases generated according to the invention still had a low but detectable recombination activity on loxP, loxH or lox LTR 1.0, no such recombination activity was detectably with the recombinases of SEQ ID NO: 11-13, as shown in the examples. The invention thus provides a well-tolerated and highly specific tailored recombinase capable of recombining asymmetric target sequences within the LTR of proviral DNA of a plurality of retrovirus strains which may be inserted into the genome of a host cell (i.e., a functional tailored recombinase), which preferably comprises SEQ ID NO:11-13, preferably, SEQ ID NO:11. Such a tailored recombinase is e.g. obtainable according to the method of the invention.

In one embodiment, the tailored recombinase may comprise a sequence according to SEQ ID NO:10. This sequence, Tre 3.1 consensus sequence 100% (3 clones) is a consensus sequence of the three preferred recombinases of SEQ ID NO:11-13.

The tailored recombinase may also have at least 95% amino acid identity, preferably, at least 99% amino acid identity or 100% amino acid identity to SEQ ID NO: 10, or it may vary from SEQ ID NO: 10 in only one or two amino acids, and it comprises the following defined amino acids exchanges as compared to the Cre sequence (SEQ ID NO: 6): V7L, P12S, P15L, M30V, H40R, M44V, S51T, Y77H, K86N, Q89L, G93A, S108G, C155G, A175S, A249V, R259D, E262R, T268A, D278G, P307A, N317T, I320S. It may also comprise the exchanges: N160T, R241Q, K244I, N319E. Preferably, it comprises the following amino acid exchanges compared to Cre: N3I, V7L, N10S, P12S, P15L, V23A, M30V, F31L, H40R, M44V, S51T, Y77H, K86N, Q89L, G93A, S102F, S108G, N111D, K122R, A131T, S147A, D153E, C155G, N160T, F163L, I166V, I174V, A175S, V182I, G198S, D232S, R241Q, K244I, A249V, Q255R, R259D, A260V, E262R, G263K, T268A, D278G, P307A, N317T, N319E, I320S.

These specific exchanges render the enzyme particularly suited for recombination at a target sequence of SEQ ID NO: 1 or a target sequence having a high sequence identity to SEQ ID NO: 1 (e.g., at least 80%, at least 90% or at least 95% sequence identity to SEQ ID NO: 1). The inventors could surprisingly show that a single amino acid variation, namely, Q89L, ensures that the tailored recombinase is both well tolerated in human cells, e.g., human hematopoietic cells or human T cells, and has high specificity, as it does not have any detectable activity in recombining the original target sequence, loxP or loxH and, preferably, also no detectable activity on loxLTR Tre 1. The activity can be detected by gel electrophoresis of a sample comprising loxP (SEQ ID NO:4), loxH (SEQ ID NO:5), or, for comparison, loxLTR Tre 3 comprising SEQ ID NO:1, each contacted with the tailored recombinase, e.g., by induction of expression thereof from a suitable vector, as shown in the examples and in FIG. 3. As can be seen in said figure, Tre 3.0 recombinase (produced according to WO 2011/147590), while already rather specific compared to other recombinases, has residual activity on loxP and loxH under the conditions shown, whereas, with uTre, a recombinase of the present invention, recombinated product can only be seen for loxLTR comprising SEQ ID NO: 1. This high specificity minimizes the risk of undesired recombination in the human genome.

The sequence of the tailored recombinase of the invention is not disclosed in WO 2008/083931 or WO 2011/147590. In particular, the prior art does not teach or suggest that a tailored recombinase capable of recombining the asymmetric target sequence of SEQ ID NO: 1 has an amino acid exchange Q89L. In contrast, WO 2011/147590 explicitly teaches that this position should be maintained as Q (see all specific sequences or consensus sequences of said publication). The sequence of the tailored recombinase of the invention also varies from the naturally occurring recombinases such as Cre, Dre, Fre or Zre, which is evident from the feature that it is capable of recombining asymmetric target sequences, preferably, SEQ ID NO: 1, within the LTR of proviral DNA of a plurality of retrovirus strains which may be inserted into the genome of a host cell.

If the tailored recombinase capable of recombining asymmetric target sequences within the LTR of proviral DNA of a plurality of retrovirus strains inserted into the genome of a host cell is to recombine the target sequence of SEQ ID NO: 1, it preferably comprises the consensus sequences Tre 3.1 85%, SEQ ID NO: 9, or Tre 3.1 consensus sequence 100%, SEQ ID NO: 10, or one of the specific sequences SEQ ID NO: 11-13.

Functional tailored recombinases capable of recombining asymmetric target sequences within the LTR of proviral DNA of a plurality of retrovirus strains which may be inserted into the genome of a host cell, which may, e.g., be obtained by the method of the invention, may vary from said sequences, but the sequences provide valuable guidance to the skilled person to produce a tailored recombinase capable of recombining asymmetric target sides, such as SEQ ID NO: 1, even without carrying out the method of the invention.

Preferably, amino acid exchanges with regard to the reference sequence are conservative substitutions, which are well known to the skilled person (eg. Creighton (1984), Proteins. W. H. Freeman and Company (Ed.)). For example, conservative substitutions substitute one amino acid from the group of negatively charged amino acids by another. Most preferably, the exchanges lead to one of the amino acids present in any of SEQ ID NO:11-13 in the relevant position.

The tailored recombinases capable of recombining asymmetric target sequences within the LTR of proviral DNA of a plurality of retrovirus strains which may be inserted into the genome of a host cell may also comprise a combination of 2 or more sequences selected from the group consisting of SEQ ID NO:11-13, e.g., a C-terminal part of any of these sequences, e.g., SEQ ID NO:11, and the N-terminal part of any other of these sequences, e.g., SEQ ID NO:12. The C-terminal part may have a length of 1-342 amino acids. In a combination of two sequences, the N-terminal part may have a length of 1-342 amino acids. The tailored recombinase may also be a combination of three or more parts derived from these sequences. The combination comprises a TRE 3.1 consensus motif, e.g., SEQ ID NO:10, or preferably, SEQ ID NO:9.

The invention also provides a nucleic acid encoding a tailored recombinase capable of re-combining asymmetric target sequences such as SEQ ID NO: 1 within the LTR of proviral DNA of a plurality of retrovirus strains which may be inserted into the genome of a host cell, the tailored recombinase comprising an amino acid sequence as defined above.

In the context of the invention, a nucleic acid or a protein comprising a sequence may consist of said sequence.

It may alternatively comprise further sequences, e.g., a signal sequence providing for expression/localization in a specific cellular compartment such as a nuclear localization signal, as in SEQ Id NO:14 (the nuclear localization signal is in positions 2-9 of SEQ ID NO:14), a. If a protein is to be used in a pharmaceutical composition, it is especially preferred to express it as a fusion protein with a protein transduction domain such as the tat protein transduction domain, which allows for protein transduction of target cells. Preferably, a tailored recombinase of the invention which is to be used in a pharmaceutical composition is prepared as a fusion protein with a nuclear localization sequence and with a protein transduction domain e g from tat, and a nucleic acid encoding a tailored recombinase of the invention may encode such a fusion protein. For example, the following protein transduction domains may be used in a fusion protein with a tailored recombinase of the invention, which preferably further includes a nuclear localization signal:

Basic domain of HIV-1 Tat transactivator (Fawell S, Seery J, Daikh Y, Moore C, Chen L L, Pepinsky B, Barsoum J., Tat-mediated delivery of heterologous proteins into cells. Proc Natl Acad Sci USA. 1994 Jan. 18; 91(2): 664-8.)

Homeodomain of Drosohila antennapedia (Antp) (Derossi D, Joliot A H, Chassaing G, Pro-chiantz A. The third helix of the Antennapedia homeodomain translocates through biological membranes. J Biol Chem. 1994 Apr. 8; 269(14): 10444-50.)

HSV VP22 transcription factor (Elliott G, O'Hare P., Intercellular trafficking and protein delivery by a herpesvirus structural protein, Cell. 1997 Jan. 24; 88(2): 223-33.)—Cell permeable translocation motif (TLM) of PreS2 surface antigen of Hepatitis B virus (HBV) (Oess S, Hildt E., Novel cell permeable motif derived from the PreS2-domain of hepatitis-B virus surface antigens, Gene Ther. 2000 May; 7(9):750-8.).

In case the protein is to be purified, a tag facilitating purification of a protein such as a His tag, may also be added.

The codon usage of the nucleic acid of the invention encoding a Tre recombinase as defined above can be chosen by the skilled person. For example, a codon usage suitable for expression in a human cell may be chosen, in particular, if expression in a human cell is intended, e.g., for therapeutical purposes. Codon usage may also be based on codon usage of e.g., Cre recombinase.

The tailored recombinase or nucleic acid encoding said tailored recombinase may be obtained by the method of the invention as described herein, or it may be obtainable by this method. It may also be obtained based on the sequences disclosed herein, optionally, by combining and/or further varying these sequences, optionally testing for activity in recombination of asymmetric target sites, such as SEQ ID NO:1.

The invention further provides for a composition, e.g., a library, comprising two or more of the nucleic acids encoding a tailored recombinase as defined above, e.g., encoding two or more tailored recombinases comprising different sequences according to SEQ ID NO:9, preferably, according to SEQ ID NO:10 or any of SEQ ID NO:11-13. In one embodiment, the composition comprises nucleic acids encoding tailored recombinases comprising two or more, three or more, four or more, five or more, ten or more, 20 or more or 25 or more recombinases comprising sequences according to any of SEQ ID NO:9-13 or combinations of these sequences. Such compositions, in particular compositions wherein the nucleic acid is an expression vector, may be particularly suitable as pharmaceutical compositions as described below.

In the method of the present invention, the nucleic acid encoding a tailored recombinase that is active on the asymmetric target sequence within the LTR of the retroviral DNA is preferably cloned into an expression vector. Expression vectors are genetic constructs for expressing the proteins encoded by the nucleic acids within the vector. Such expression vectors may be either self-replicating extrachromosomal vectors or vectors which integrate into a host genome. Generally, these expression vectors include transcriptional and translational regulatory nucleic acid operably linked to the nucleic acid encoding the tailored recombinase of the present invention.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do not exist, synthetic oligonucleotide adaptors or linkers are used in accordance with conventional practice. The transcriptional and translational regulatory nucleic acid will generally be appropriate to the host cell used to express the tailored recombinase. Numerous types of appropriate expression vectors, and suitable regulatory sequences are known in the art for a variety of host cells.

The expression vector used in the present invention may be a retroviral vector, a lentiviral vector, a spumavirus vector, an adenoviral vector, or an adeno-associated virus vector. However, in a preferred embodiment the expression vector is a lentiviral vector selected from the group consisting of HIV-1-, SIV-, FIV- or EIAV-derived lentiviral vectors. Lentiviral vectors are for example described by SCHAMBACH et al. (2006) or in European Patent Application No. 1 1000751.5.

In preferred embodiments of the present invention the expression vector comprises a cellular, bacterial, a viral or a hybrid promoter.

In general, for the purpose of the present invention, the promoter may be a constitutive or an inducible promoter. Further, the promoters may be either a naturally occurring promoter, such as a bacterial, cellular or a viral promoter, or a hybrid promoter. Hybrid promoters, which combine elements of more than one promoter, are known in the art, and are useful in the present invention. Further, the promoter used in the present invention may also be a derivative of a naturally occurring promoter. A "derivative" of a naturally occurring promoter as used herein may be a combination of cis-active elements obtained from promoters or sequences of different origin or, alternatively, may be obtained by deletion or mutation of cis-active elements within a specific naturally occurring promoter (EDELMAN et al, 2000; ALPER et al, 2006; HARTENBACH & FUSSENEGGER, 2006).

In an embodiment of the present invention, the constitutive promoter or derivative thereof is selected or derived from the group consisting of promoters of cytomegalovirus, Rous sarcoma virus, murine leukemia virus-related retroviruses, phosphoglycerokinase gene, murine spleen focus-forming virus or human elongation factor 1 alpha.

In a further embodiment of the present invention, the inducible promoter or derivative thereof is selected or derived from the group consisting of the LTR or derivatives thereof derived from lentiviruses, spumaviruses and deltaretroviruses.

In this context, the term "LTR" refers to both the 5' and the 3' long terminal repeats of provirus having promoter function (for a review see the standard textbook "Retroviruses" (COFFIN J M, HUGHES S H, VARMUS HE (Eds.) 1997, Cold Spring Harbor Laboratory Press, New York)).

Preferably, the inducible promoter or derivative thereof is selected or derived from the LTR or derivatives thereof derived from HIV-1, HIV-2, MVV, EIAV, CAEV, SIV, FIV, BIV, HTLV-I and HTLV-II.

The present invention further provides a method for preparing a tailored recombinase, wherein said method comprises the aforementioned method for preparing an expression vector encoding a tailored recombinase, and the further step of expressing said tailored recombinase (or a fusion polypeptide comprising the amino acid sequence of said tailored recombinase) from said expression vector in a suitable host cell.

Preferably, the recombinases finally obtained are tested in mammalian cells to ensure that they function in a mammalian cell environment. Further, to obtain good expression in mammalian cells the recombinases may be optimized for expression in these cells (e.g. codon usage optimization using methods well known in the art. See for example SHIMSHE et al, 2002) or signal sequences necessary for directing the protein into the nucleus of the mammalian cell, such as the NLS sequence (MACARA, 2001) may be added to the nucleic acid of the tailored recombinase. Expression of the nucleic acid encoding the tailored recombinase cloned into an expression vector, e.g., according to step (1) of the method for preparing an expression vector encoding a tailored recombinase, can be carried out using for example bacterial, insect or mammalian expression systems. However, other expression systems known in the art may also be employed. Methods of introducing exogenous nucleic acid into mammalian, insect or bacterial hosts, as well as other hosts, are also well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

Fusion proteins are prepared by methods well known in the art. For example, the expression vector into which the nucleic acid encoding the tailored recombinase is cloned already comprises a nucleic sequence encoding a second polypeptide or protein. By cloning the nucleic acid encoding the tailored recombinase in frame with the sequence of the second polypeptide or protein, both sequences will be expressed as fusion protein.

The host cells used for expressing the tailored recombinase from the expression vector are include prokaryotic cells, such as for example bacterial cells or yeast cells, or, preferably, eukaryotic cells, such as for example insect cells or mammalian, most preferably, human cells. The host cell may be a hematopoietic cell, e.g., an adult hematopoietic stem cell or a T-cell, e.g., a CD4+ cell. The cell may be derived from a subject infected with the retrovirus, and the cell may be administered back to the subject after transformation, and, optionally, cultivation and/or propagation.

The present invention further provides a method for preparing a transformed adult stem cell, wherein said method comprises the aforementioned method for preparing an expression vector encoding a tailored recombinase and the further step of introducing the expression vector obtained in the aforementioned method for preparing en expression vector encoding a tailored recombinase in vitro into a suitable adult stem cell.

In a further aspect, the present invention is directed to the nucleic acid as disclosed herein, and/or as obtainable from the aforementioned method of the present invention. Nucleic acids encoding a tailored recombinase defined by a sequence are also provided herein.

A "nucleic acid" as used herein is a polymeric compound comprised of covalently linked sub-units called nucleotides. Nucleic acid includes polyribonucleic acid (RNA), e.g., mRNA, and polydeoxyribonucleic acid (DNA), both of which may be single-stranded or double-stranded. DNA includes cDNA, genomic DNA, synthetic DNA, and semi-synthetic DNA.

In a further aspect, the present invention is also directed to the expression vector as obtainable from the aforementioned method of the present invention, and to an expression vector comprising the nucleic acid encoding a tailored recombinase as defined herein.

The term "protein" as used herein includes proteins, polypeptides, and peptides. As will be appreciated by those in the art, the nucleic acid sequences of the invention can be used to generate protein sequences. A further aspect of the invention is the tailored recombinase protein as obtainable, e.g., from the aforementioned method of the present invention, which recombinase may optionally be a fusion protein comprising a functional recombinase. In one embodiment, the tailored recombinase protein may be prepared as a fusion polypeptide, using techniques well known in the art. In a preferred embodiment, the tailored recombinase protein is linked to a second polypeptide. Preferably the fusion polypeptide is obtained from the aforementioned method of the present invention, wherein the tailored recombinase is linked to a second polypeptide.

In one embodiment, the tailored recombinase protein is prepared as a fusion polypeptide to increase expression. In a further embodiment, the tailored recombinase protein is made as a fusion polypeptide to allow introduction of the polypeptide into living cells. Typically, purified proteins cannot enter into cells, because they are not able to pass the cell membrane due to their size. However, fusion of specific peptides sequences to proteins can result in the uptake of these fusion proteins into cells. In the cell the protein can then perform its function. Site specific recombinases, including Cre recombinase, have been successfully delivered into cells with this approach (PEITZ et al., 2002). Cell-permeant recombinases have further been described by NOLDEN et al. (2006) and LIN et al. (2004). Hence, this strategy may be used to deliver the tailored recombinases into cells to remove the provirus from infected cells. Thus, the second polypeptide in the fusion polypeptide may comprise a signal peptide. The signal peptide may be a protein transduction domain such as the TAT peptide or a peptide from the third helix of the Antennapedia homeodomain (DEROSSI et al, 1994, 1996; VIVES et al, 1997; VIVES, 2003; RICHARD et al, 2005) or the NLS (nucleus localization sequence) for delivering the fusion polypeptide into the nucleus of an eukaryotic cell (MACARA, 2001).

A further aspect of the present invention is directed to the adult stem cell as obtainable from the aforementioned method for preparing a transformed adult stem cell of the present invention. The stem cells are preferably infected or transfected with the expression vector according to the invention. In a preferred embodiment, the adult stem cell is a stem cell from the hematopoietic lineage expressing the tailored recombinase, the aforementioned fusion polypeptide or comprising the aforementioned expression vector. Hematopoietic stem cells (HSC) are bone marrow-derived CD34+ cells, which can, e.g., be purified from G-CSF-mobilized peripheral blood of donors (e.g., HIV-infected patients) by routine leukapheresis (SCHERR & EDER, 2002). The in vitro genetically modified cells may then be formulated for reinfusion into the patients.

In the state of the art, the term "stem cells" designates cells which (a) have the capability of self-renewal and (b) the capability to form at least one and often a number of specialized cell types due to their asymmetrical division capability (DONOVAN & GEARHART, 2001). Adult stem cells can be isolated from different tissues of adult, i.e. from differentiated individuals. Such stem cells are referred to in the state of the art as "multipotent adult stem cells". The essential difference between embryonic pluripotent stem cells and adult multipotent stem cells lies in the number of differentiated tissues which can be obtained from the respective cells.

In a further embodiment, the expression vector of the present invention is used for transforming T-cells, e.g., CD4+ primary cells (blood cells) of retrovirus (e.g., HIV)-infected patients.

Alternatively, the tailored recombinase of the invention may be formulated for delivery by virus-like particles (VLPs). VLPs can be used to package Tre mRNA, Tre protein, e.g., fusion protein, or DNA, e.g., Tre expressing DNA plasmids, or a construct comprising Promotor-Tre cDNA-polyA site. Accordingly, the nucleic acid of the invention may further contain a packaging signal.

In a further step of the method of the present invention, the nucleic acid of the invention, the expression vector comprising the nucleic acid sequence encoding a tailored recombinase of the invention, the recombinase protein, the fusion protein or the adult stem cell obtained by the methods of the present invention are formulated as a pharmaceutical composition for use in prevention and/or treatment of a retrovirus infection and/or for the reduction of the viral load in a subject infected by a retrovirus, e.g., HIV, in particular, HIV-1. A further object of the invention is the pharmaceutical composition obtained by the aforementioned method. The pharmaceutical composition is preferably present in the form of a solution suitable for intravenous application (infusion).

The pharmaceutical preparation may further comprise one or more pharmaceutically acceptable carrier(s), excipient(s) and/or adjuvant(s). Carriers, excipients and adjuvants suitable for use in a pharmaceutical composition are known in the art.

The pharmaceutical composition of the present invention preferably reduces the virus load in a subject infected by a retrovirus below 5.000 genome equivalents/ml plasma, preferably below 500 genome equivalents/ml plasma and more preferably below 50 genome equivalents/ml plasma when administered to the subject. Thus, the pharmaceutical composition of the present invention comprising an expression vector encoding a tailored recombinase (or the tailored recombinase as a protein or fusion polypeptide or a stem cell comprising the expression vector) is capable of reducing the virus load in a subject infected with a retrovirus by eradicating the genetic reservoir of retroviruses within hosts cells, thereby preventing further life cycles of the virus.

The term "virus load" as used herein refers, e.g., to the HIV RNA equivalents (i.e. genomes) that are associated with 1 ml of the patient's plasma (DYBUL et al, 2002). Thus, the virus load is determined by measuring the content of viral DNA in a sample obtained from the patient. Currently, there are three main types of viral load assays available:
1) HIV RNA reverse transcription-polymerase chain reaction (RT-PCR): Amplicor™ HIV-1 Monitor Test; Roche Diagnostics
2) Branched chain DNA (bDNA): Versant™ HIV RNA Assay; Bayer Diagnostics; and
3) Nucleic acid sequence-based amplification (NASBA): NucliSens™ Assay; bioMerieux.

In a preferred embodiment, the pharmaceutical composition of the present invention is capable of reducing the virus load in a subject infected by a retrovirus below 5.000 genome equivalents/ml plasma, preferably below 500 genome equivalents/ml plasma and more preferably below 50 genome equivalents/ml plasma. Patient with a virus load of below 5000 genome equivalents/ml plasma are considered to be relatively well adjusted to the medicinal treatment. However, the goal in current AIDS therapy is a reduction of the viral load below the detection limit of the virus load assays, which is currently below about 50 genome equivalents/ml plasma. The pharmaceutical composition preferably reduces the viral load of retroviruses selected from the group consisting of the Mouse mammary tumour virus (MMTV), Mason Pfizer monkey virus (MPMV), Human T cell leukemia virus Type I (HTLV-I), Human T cell leukemia virus Type II (HTLV-II), Simian T cell leukemia virus Type I (STLV-I), Simian T cell leukemia virus Type II (STLV-II), Bovine leukemia virus (BLV), Feline leukemia virus (FeLV) and Moloney murine leukemia virus (MoMLV). In yet a further preferred embodiment retrovirus to be treated with the pharmaceutical of the present invention is a lentivirus. Said lentivirus is preferably selected from the group consisting of Human immunodeficiency virus Type 1 (HIV-1), Human immunodeficiency virus Type 2 (HIV-2), Simian immunodeficiency virus (SIV), Feline immunodeficiency virus (FIV), Bovine immunodeficiency virus (BIV), Maedi-visna virus (MVV), Equine infectious anemia virus (EIAV) and Caprine arthritis encephalitis virus (CAEV). Most preferably, the retrovirus is HIV, in particular HIV-1. However, it is obvious to the person skilled in the art that the present invention is also applicable to retroviral infections by other retroviruses than those mentioned above.

The subject infected by a retrovirus, to whom the pharmaceutical composition is to be administered, is selected from the group consisting of humans, primates, monkeys, cattle, horses, goats, sheep and domestic cats. However, the subject is preferably a human being.

In general, an effective amount of the expression vector, the tailored recombinase or the transformed cell of the invention is to be administered to the subject. Administration may be, e.g., intravenous or intramuscular administration.

In one embodiment, the pharmaceutical composition is formulated for concomitant administration with other active agents of the highly active antiretroviral therapy (HAART). The highly active antiretroviral therapy HAART is a combination therapy targeting the viral reverse transcriptase, protease and fusion (GULIC et al, 1997; LALEZARI et al, 2003).

In another embodiment, the pharmaceutical composition is formulated for administration concomitant or subsequent to global immune activation therapy or specific activation of provirus gene expression. The premise of immune activation therapy is based on the hypothesis that deliberate activation of latently HIV-infected cells may accelerate eradication of persistent viral reservoirs. Eradication would occur via immune clearance by programmed death of those cells actively expressing HIV-1 (pro-apoptotic) products (KULKOSKY & BRAY, 2006). Global immune activation (activation of immune cells, including resting cells) is usually achieved by, for example, administration of immunotoxins, cytokines (e.g., IL-2), or T cell activating antibodies (e.g., OKT3).

In view of the fact that immune activation conducted to deliberately activate HAART-resistant latent reservoirs did unfortunately fail to permanently eliminate HIV-1 and viral rebound (for reviews see KULOSKY & BRAY 2006; MARCELLO, 2006; SHEHU-XHILAGA et al, 2005) due to the fact that global T cell activation apparently also induces viral replication and increases the number of potential HIV-1 target cells beyond the level that can be contained by HAART (FRASER et al, 2000), further specific treatments are necessary to treat HIV. One approach is the activation of transcription of otherwise quiescent viral genomes. Specific activation of latent provirus gene expression may be achieved by administration of the phorbol ester prostratin or the human cytokine IL-7, which both appear to reactivate latent HIV-1 in the absence of cellular proliferation (MARCELLO, 2006). Moreover, the selective transcriptional activation of HIV-1 may also be achieved by histone-deacetylase (HDAC1)-inhibitors such as, for example, valproic acid, that eventually induces outgrowth of HIV-1 from resting cells in absence of cellular activation (MARCELLO, 2006; LEHRMAN et al, 2005).

However, global immune activation therapy or specific activation of provirus gene expression or similar therapy strategies greatly benefits from the concurrent removal of proviral DNA, thereby reducing in the patient the pool of infected cells.

The present invention also provides a method of treatment and/or prevention of a retrovirus infection, in particular, an HIV infection, in a subject. In one embodiment, the sequence of the retrovirus infecting the subject is analyzed in a sample obtained from the subject, and at least one expression vector encoding a tailored recombinase, at least one tailored recombinase or at least one cell transformed with said expression vector, e.g., one adult stem cell, is to be administered to the subject, if the proviral DNA from the subject comprises the asymmetric target sequence identified in step (a) on which the recombinase has been selected. The sample obtained from the subject may be a blood sample, e.g., comprising infected CD4+ cells.

BRIEF DESCRIPTION OF THE FIGURES

FIG. 1: FIG. 1 provides an alignment of the protein sequences of (a) Cre recombinase SEQ ID NO:6;
(b) Tre common consensus sequence, SEQ ID NO:7, consensus sequence of Tre recombinases specific for asymmetric target-sites within HIV-1 LTR according to WO 2011/147590;
(c) Tre recombinase 3.0 consensus sequence, SEQ ID NO:8, Tre recombinases specific for SEQ ID NO:1 according to WO 2011/147590;
(d) Tre recombinases 3.1 consensus sequence 85%, SEQ ID NO:9, the individual mutations in the consensus sequence versus the Cre sequence are present in 85% of all clones generated by the method of the present invention and analyzed by high-throughput sequencing (33,000 reads of unique 200 bp-sequences);
(e) Tre recombinase 3.1 consensus sequence 100%, SEQ ID NO:10, consensus sequence of three Tre recombinases 3.1 selected for high specificity for SEQ ID NO:1 (no activity on loxP, loxH or loxLTR Tre 1.0 (SEQ ID NOs: 3-5) and tolerability by humans; and
(f) exemplary Tre 3.1 recombinase uTre, SEQ ID NO:11, highly specific for SEQ ID NO:1 and well-tolerated by humans. The tailored recombinase according to this sequence is designated uTre, respectively "universal Tre".

Bold letter patches indicate conserved amino acids, variable and non-specified positions are indicated with an X. Positions of Cre mutated in SEQ ID NO: 9. 10 and/or 11 are underlined in the Cre sequence, and the position of the mutation is provided above the sequences. The Q89L exchange uniquely found in Tre3.1 is marked in italics.

Figure 2:
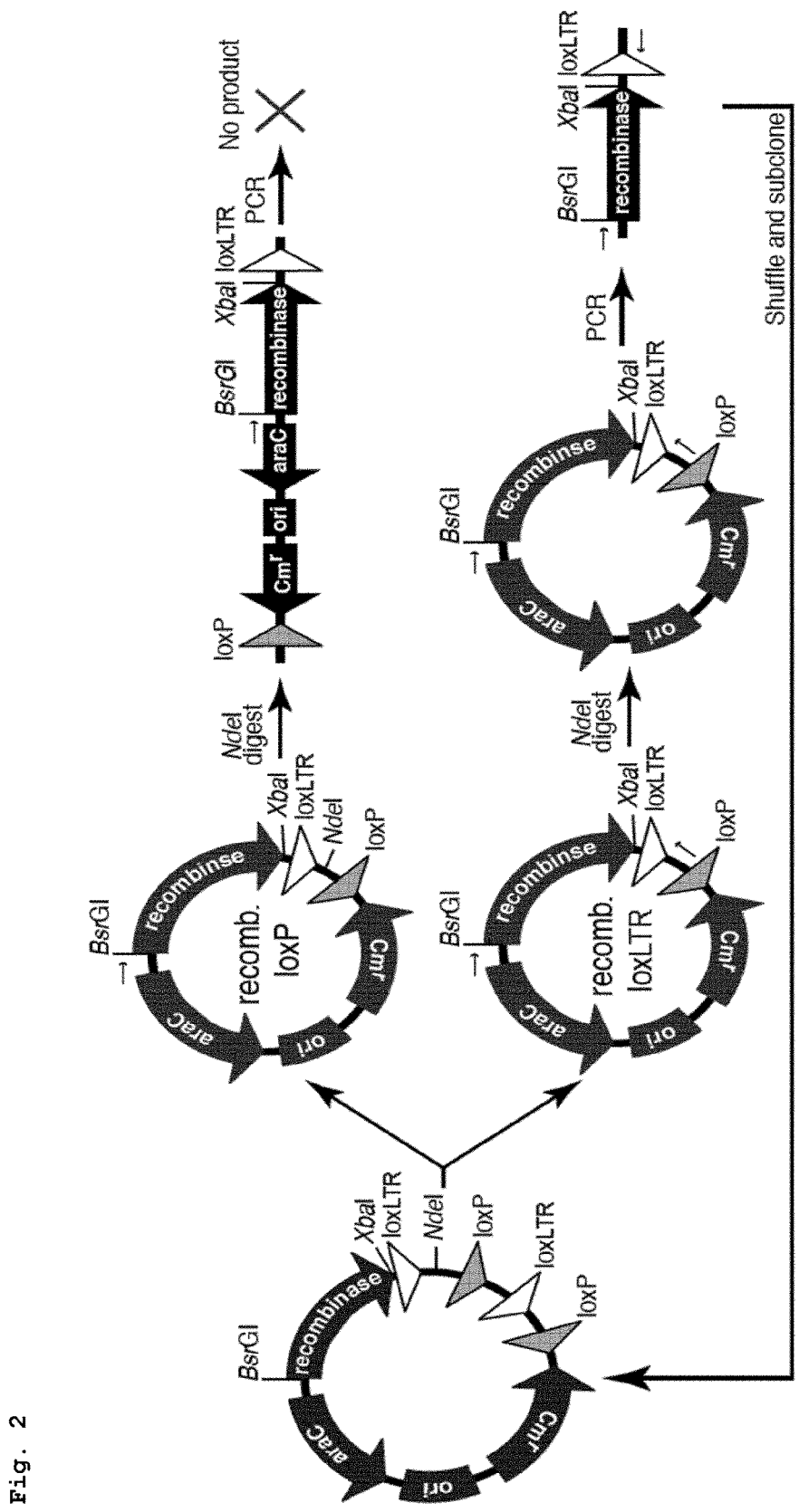

FIG. 2: FIG. 2 shows an exemplary evolution vector for evolutionary selecting against recombination on loxP. Corresponding vectors for selecting against recombination on loxH can easily be constructed. loxLTR comprises SEQ ID NO: 1. Tre3 evolution cycles 51-69 were performed with pEVOloxLTR-loxP and pEVOloxLTR-loxH, alternately, 100-1 µg/mL of the transcription activator L-ara, including two rounds of DNA shuffling).

Figure 3:
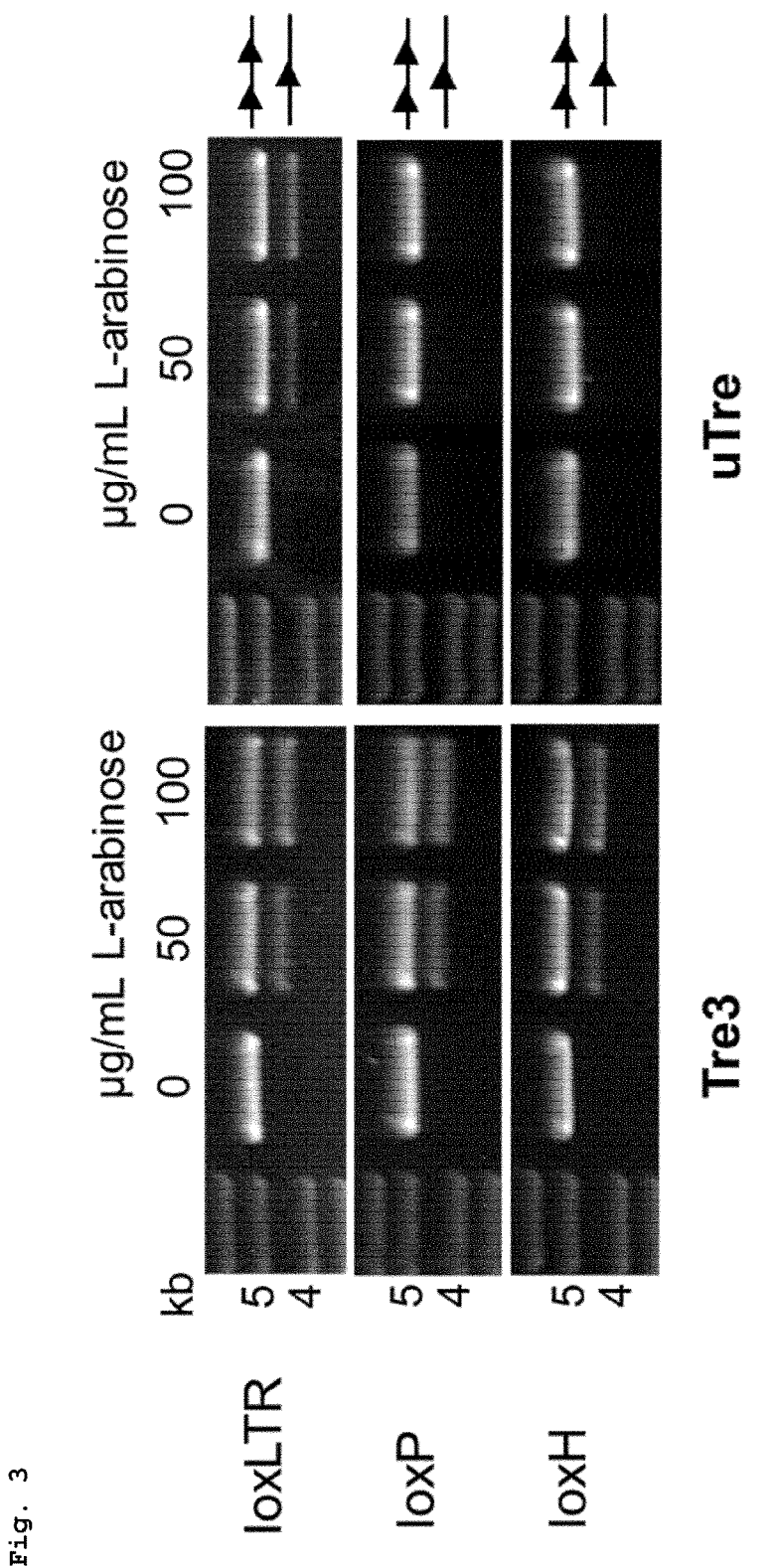

FIG. 3: FIG. 3 shows the high specificity of uTre vs. Tre3. Tre3: Clone was isolated from Tre3.0 library cycle 43. uTre: Clone was isolated from Tre3.1 library cycle 71. Recombined product is marked with one triangle, non-recombined with two triangles. Under conditions where the tailored recombinase is expressed (induction by L-arabinose), uTre recombines loxLTR comprising SEQ ID NO: 1 in E. coli. In contrast, Tre3 recombines loxLTR and loxP and loxH, i.e., it has a relatively relaxed specificity.

Figure 4:
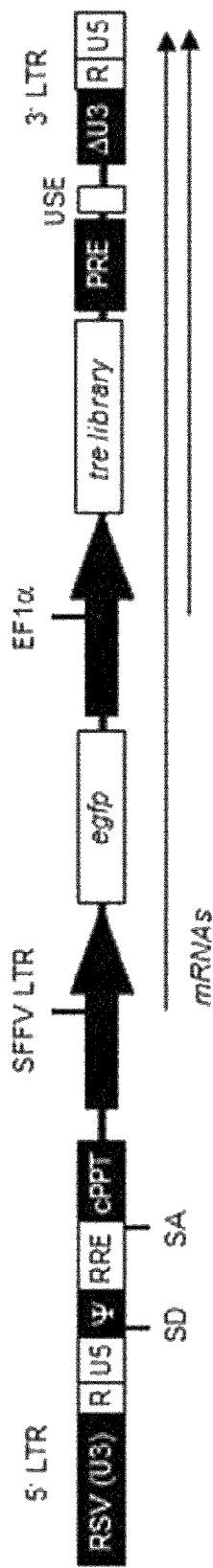
Figure 4:
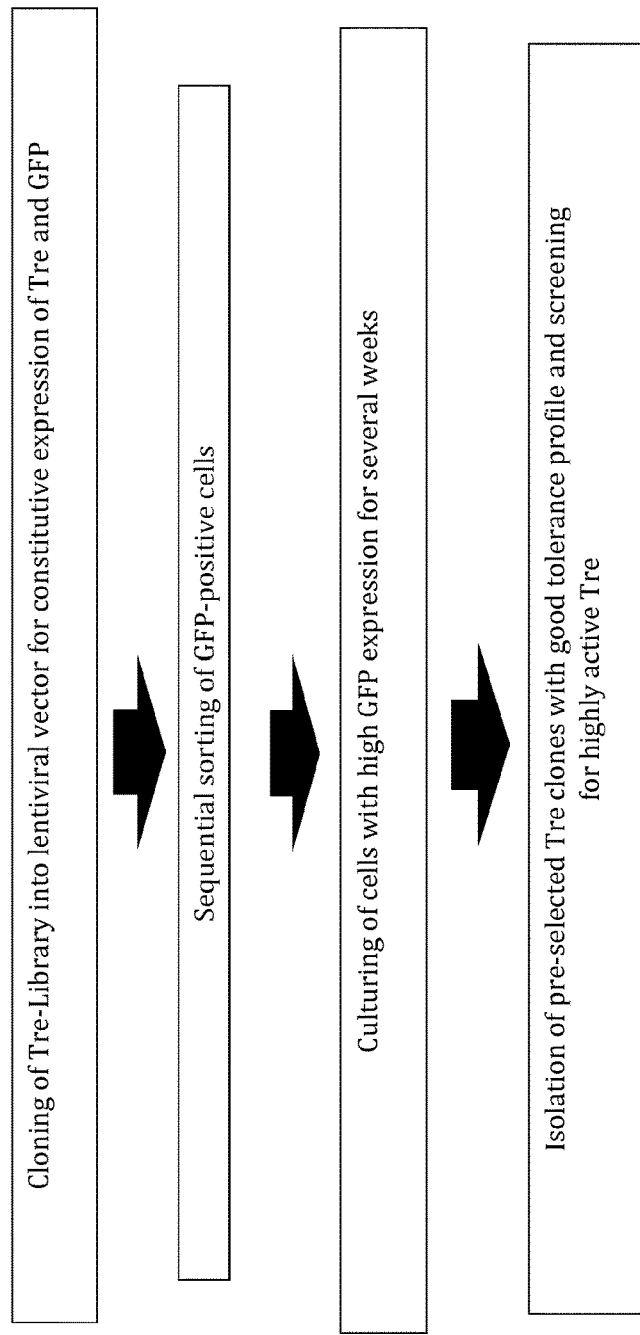

FIG. 4: FIG. 4A shows an exemplary lentiviral expression vector for constitutive expression of a selectable marker, EGFP, and the tre library in human cells. FIG. 4B shows the flow scheme for the cellular screening for well-tolerable highly specific Tre. The final screening for highly active Tre confirms activity in the human cells. Single clones of recombinases were selected and were subjected to further analyses.

Figure 5B:
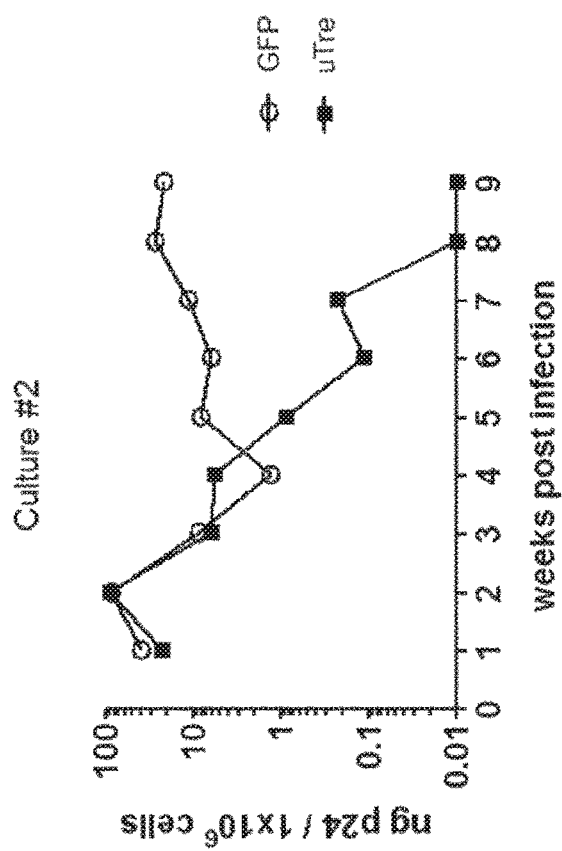
Figure 5A:
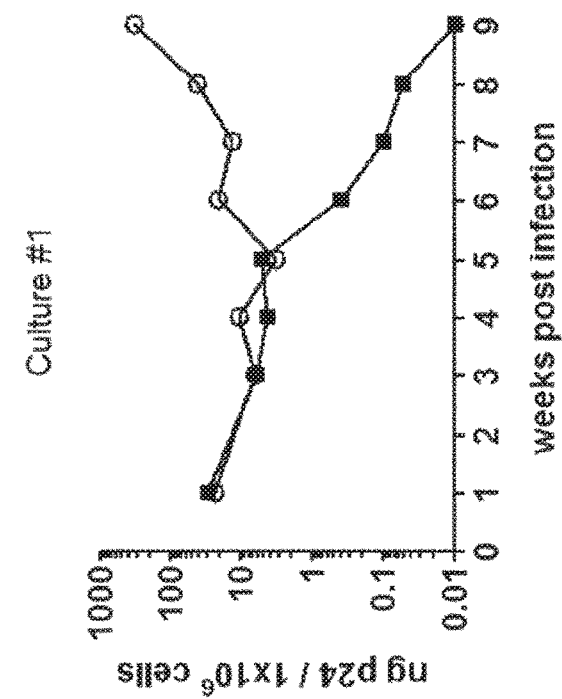

FIGS. 5A-5B show antiviral uTre activity in tissue culture in two representative cultures. PM1 T cells were transduced with vectors encoding GFP alone (Control, open circles) or encoding uTre and GFP (uTre, filled squares). Subsequently, cultures were infected with HIV-1 and viral load was monitored over time using p24 Antigen ELISA. The experiment shows that the tailored recombinase is efficient in reducing viral load. After several weeks (8 or 9 weeks), viral load is not any more detectable by a p24 antigen ELISA.

Figure 6:
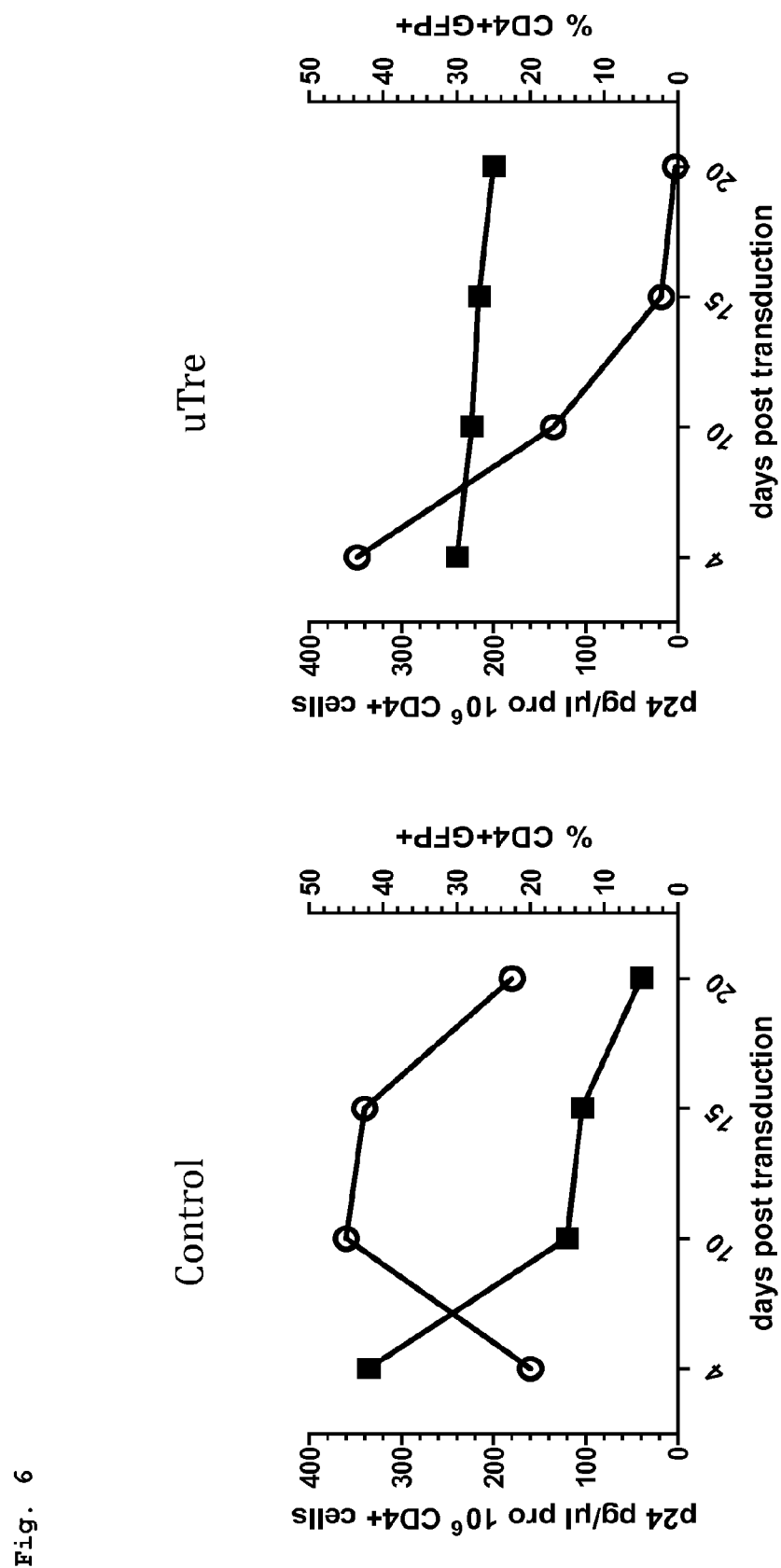

FIG. 6 Pronounced antiviral uTre activity in primary human CD4+ cells derived from a HIV-infected patient is shown. Cells were transduced with a vector expressing GFP alone (Control experiment; left panel) or with a vector expressing uTre and GFP (uTre; right panel). Virus replication was monitored by HIV-1 p24 antigen release (open circles) and percent of transduced (GFP+) human CD4+ cells (filled squares) was monitored by FACS. Expression of uTre resulted in pronounced antiviral effect and protection of CD4+ cells. Of note, the decline in viral load between day 15 and day 20 in the control experiment reflects cell death due to uninhibited virus replication.

FIG. 7 shows antiviral uTre activity in HIV-infected humanized mice Immunodeficient mice were engrafted with human CD34+ hematopoietic stem cells/HSC (Control), or with uTre-expressing CD34+ HSC (Animal/41 and #2). Subsequently, animals were HIV-1 infected and viral load (detected as HIV-1 RNA copies/ml; open circles) and the percentage of human CD45+CD4+ cells of all lymphocytes (filled squares) were monitored over time.

EXAMPLES

Example 1

Materials and methods as described in WO 2008/083931, WO 2011/147590 and BUCHHOLZ & STEWART, 2001 are used, if not specified otherwise. Tailored recombinases capable of recombining asymmetric target sequences in a plurality of different HIV-1 strains were prepared as described in WO 2011/147590. The resulting tre libraries were employed in further experiments.

Example 2

To enhance uTre specificity, additional evolution cycles selecting against recombination activity on loxP and loxH were performed. For this purpose the evolved Tre library obtained from evolution cycle 50 was cloned into an evolution vector containing the two loxLTR sites (SEQ ID NO: 1) intertwined with two loxP sites or two loxH sites, respectively. An exemplary vector is shown in FIG. 2. Upon induction of recombinase expression, recombination on loxLTR resulted in the removal of the only present NdeI site whereas recombination on loxP or loxH did not. Plasmid DNA isolated after each evolution cycle was digested with NdeI and the recombinase coding sequences that had successfully recombined loxLTR rather than loxP or loxH were amplified by PCR and subcloned back into the evolution vector for the next evolution cycle. A total of 19 additional Tre3 evolution cycles, including two rounds of DNA shuffling, were performed, alternately selecting against recombination on loxP and loxH.

Example 3

To screen for uTre-recombinases with significantly diminished cell toxicity (i.e. cytopathicity), the tre libraries were ligated into a lentiviral vector that constituively expresses EGFP from an internal SFFV LTR promoter and the tre library from the constitutive EF1alpha promoter (FIG. 4A). Transduction of Jurkat T cells allowed the sequential sorting (by FACS) of high GFP-expressing cells and subsequent isolation of non-toxic uTre clones (FIG. 4B). For this, cell sorts on the transduced T cell cultures were performed at day 3, day 10 and day 24 post transduction with increased stringency on EGFP expression. After another week of culturing, the remaining tre library was isolated and selected clones were analyzed with respect to enhanced Tre activity.

Example 4

To analyze uTre activity in cell lines, cultures of PM-1 T cells were transduced with ASLV-derived retroviral vectors expressing either uTre and GFP, or GFP alone (negative control vector). Of note, GFP expression allowed the tracking of transduced cells. At 10 days post transduction, cells were infected with HIV-1$_{Bal}$. The effect of uTre expression on HIV-1 replication was monitored by weekly ELISA measurements of the amount of viral p24 antigen in the culture supernatants. As shown (FIG. 5), p24 release decreased remarkably in the uTre-transduced cultures, whereas it stays stable or even increases in the control cultures (expressing GFP alone).

Example 5

Analysis of uTre activity in primary CD4+ cells derived from an HIV-1-infected patient. CD4+ cells were stimulated with CD3/CD28 magnetic beads for 48 h. Subsequently, cells were transduced with lentiviral vectors either expressing GFP alone (serving as negative control) or expressing uTre together with GFP. Cells were cultured in the presence of 100 IU of IL2 for 20 days. Viral loads (measured by p24 antigen ELISA) and human transduced CD4+ cell counts (analyzed by FACS) were monitored at the indicated days post transduction. As shown in FIG. 6, uTre expression results in pronounced antiviral effect (indicated by open circles) and protection of CD4+ cells (indicated by filled squares). In contrast, decline in viral load between day 15 and day 20 in the control experiment reflects cell death due to uninhibited virus replication.

Example 6

Analysis of uTre activity in vivo. Immunodeficient NOG mice (NOD.Cg-Prkdc$^{scid}$IL2rg$^{tm1Wjl}$SzJ) were engrafted with human CD34+ hematopoietic stem cells/HSC (Control), or with uTre-expressing CD34+ HSC. Subsequently, animals were infected with HIV-1$_{Bal}$ and viral load (detected by ultrasensitive PCR-based assay) and percent human CD45+CD4+ cells (analyzed by FACS) were monitored over time. As shown (FIG. 7) uTre expression resulted in significant antiviral activities in vivo.

REFERENCE LIST

Abremski K, Hoess R H, Sternberg N (1983) "Studies on the properties of PI site-specific recombination: evidence for topologically unlinked products following recombination." Cell 32, 1301-1311.

Abremski K, Hoess R (1983) "Bacteriophage PI site-specific recombination. Purification and properties of the Cre recombinase protein." J Biol. Chem. 259, 1509-1514.

Adachi A, Gendelman H E, Koenig S, Folks T, Willey R, Rabson A, Martin M A (1986) "Production of acquired immunodeficiency syndrome-associated retrovirus in human and non-human cells transfected with an infectious molecular clone." J Virol. 59, 284-291.

Alper H, Fischer C, Nevoigt E, Stephanopoulos G (2006) "Tuning genetic control through promoter engineering" Proc. Natl. Acad. Sci. USA 102, 12678-12683.

Altschul, S. F., Madden, T. L., Schaffer, A. A., Zhang, J., Zhang, Z., Miller, W. and Lipman, D. J. (1997) Gapped BLAST and PSI-BLAST: a new generation of protein database search programs. Nucleic acids research, 25, 3389-3402.

Beyer W R, Westphal M, Ostertag W, von Laer D (2002) "Oncoretrovirus and lentivirus vectors pseudotyped with lymphocytic choriomeningitis virus glycoprotein: generation, concentration and broad host range." J Virol. 76, 1488-1495.

Blackard J T, Renjifo B R, Mwakagile D, Montano M A, Fawzi W W, Essex M (1999) "Transmission of human immunodeficiency type 1 viruses with intersubtype recombinant long terminal repeat sequences." Virology 254, 220-225.

Bloom J D, Meyer M M, Meinhold P, Otey C R, MacMillan D, Arnold F H (2005) "Evolving strategies for enzyme engineering." Curr. Opin. Struct. Biol. 15, 447-452.

Buchholz F, Ringrose L, Angrand P O, Rossi F, Stewart A F (1996) "Different thermostabilities of FLP and Cre recombinases: implications for applied site-specific recombination." Nucl. Acids Res. 24, 4256-4262.

Buchholz F, Angrand P O, Stewart A F (1998) "Improved properties of FLP recombinase evolved by cycling mutagenesis." Nat. Biotechnol. 16, 657-662.

Buchholz F, Stewart A F (2001) "Alteration of Cre recombinase site specificity by substrate-linked protein evolution." Nat. Biotechnol. 19, 1047-1052.

Chiu Y L, Soros V B, Kreisberg J F, Stopak K, Yonemoto W, Greene W C (2005) "Cellular APOBEC3G restricts HIV-1 infection in resting CD4+ T cells." Nature 435, 108-114

Chun T-W, Engel D, Berrey M M, Shea T, Corey L, Fauci A S (1998) "Early establishment of a pool of latently infected, resting CD4+ T cells during primary HIV-1 infection." Proc. Natl. Acad. Sci. USA 95, 8869-8873.

Coates C J, Kaminski J M, Summers J B, Segal D J, Miller A D, Kolb A F (2005) "Site-directed genome modification: derivatives of DNA-modifying enzymes as targeting tools." Trends Biotechnol. 23, 407-419.

Collins C H, Yokobayashi Y, Umeno D, Arnold F H, (2003) "Engineering proteins that bind, move, make and break DNA." Curr. Opin. Biotechnol. 14, 665.

Combes P, Till R, Bee S, Smith M C (2002) "The *streptomyces* genome contains multiple pseudo-attB sites for the (phi)C31-encoded site-specific recombination system." J Bacteriol. 184, 5746-5752.

Crameri A, Raillard S A, Bermudez E, Stemmer W P (1998) "DNA shuffling of a family of genes from diverse species accelerates directed evolution." Nature 391, 288-291.

Derossi D, Joliot A H, Chassaing G, Prochiantz A (1994) "The third helix of the Antennapedia homeodomain translocates through biological membranes." J Biol Chem. 269, 10444-10450.

Derossi D, Calvet S, Trembleau A, Chassaing G, Prochiantz A (1996) "Cell internalization of the third helix of the Antennapedia homeodomain is receptor-independent." J Biol Chem 271, 18188-18193.

Donovan, P. J., Gearhart, J. (2001) "The end of the beginning for pluripotent stem cells." Nature 414, 92-97.

Donzella G A, Schols D, Lin S W, Este J A, Nagashima K A, Maddon P J, Allaway G P, Sakmar T P, Henson G, De Clercq E, Moore J P (1998) "AMD3100, a small molecule inhibitor of HIV-1 entry via the CXCR4 co-receptor." Nature Medicine 4, 72-77.

Dybul M, Fauci A S, Bartlett J G, Kaplan J E, Pau A K (2002) "Guidelines for using antiretroviral agents among HIV-infected adults and adolescents." Annals of Internal Medicine 137, 381-433.

Eddy, S. R. (1998) Profile hidden Markov models. Bioinformatics (Oxford, England), 14, 755-763.

Edelman G M, Meech R, Owens G C, Jones F S (2000) "Synthetic promoter elements obtained by nucleotide sequence variation and selection for activity." Proc. Natl. Acad. Sci. USA 97, 3038-3043.

Elliott G, O'Hare P., Intercellular trafficking and protein delivery by a herpesvirus structural protein, Cell. 1997 Jan. 24; 88(2):223-33

Emerman M, Malim M H (1998) "HIV-1 regulatory/accessory genes: keys to unraveling viral and host cell biology." Science 280, 1880-1884.

Fawell S, Seery J, Daikh Y, Moore C, Chen L L, Pepinsky B, Barsoum J., Tat-mediated delivery of heterologous proteins into cells. Proc Natl Acad Sci USA. 1994 Jan. 18; 91(2):664-8.

Finzi D, Hemankova M, Pierson T, Carruth L M, Buck C, Chaisson R E, Quinn T C, Chadwick K, Margolick J, Brookmeyer R, Gallant J, Markowitz M, Ho D D, Richman D D, Siliciano R F (1997) "Identification of a reservoir for HIV-1 in patients on highly active antiretro viral therapy." Science 278, 1295-1300.

Flowers C C, Woffendin C, Petryniak J, Yang S, Nabel G J (1997) "Inhibition of recombinant human immunodeficiency virus type 1 replication by a site-specific recombinase." J. Virol. 71, 2685-2692.

Gulick R M, Mellors J W, Havlir D, Eron J J, Gonzalez C, McMahon D, Richman D D, Valentine F T, Jonas L, Meibohm A, Emini E A, Chodakewitz J A (1997) "Treatment with indinavir, zidovudine, and lamivudine in adults with human immunodeficiency virus infection and prior antiretroviral therapy." N Engl. J. Med. 337, 734-739.

Guzman L M, Belin D, Carson M J, Beckwith J (1995) "Tight regulation, modulation, and high-level expression by vectors containing the arabinose PBAD promoter." J. Bacteriol. Ill, 4121-4130.

Hartenbach S, Fussenegger M (2006) "A novel synthetic mammalian promoter derived from an internal ribosome entry site." Biotechnology and Bioengineering 95, 547-559.

Hauber I, Bevec D, Heukeshoven J, Kratzer F, Horn F, Choidas A, Harrer T, Hauber J (2005) "Identification of cellular deoxyhypusine synthase as a novel target for antiretroviral therapy." J. Clin. Invest. 115, 76-85.

Hazuda D J, Young S D, Guare J P, Anthony N J, Gomez R P, Wai J S, Vacca J P, Handt L, Motzel S L, Klein H J, Dornadula G, Danovich R M, Witmer M V, Wilson K A, Tussey L, Schleif W A, Gabryelski L S, Jin L, Miller M D, Casimiro D R, Emini E A, Shiver J W (2004) "Integrase inhibitors and cellular immunity suppress retroviral replication in rhesus macaques." Science 305, 528-532.

Hoess R H, Abremski K (1985) "Mechanism of strand cleavage and exchange in the Cre-lox site-specific recombination system." J. Mol. Biol. 181, 351-362. Johannes T W, Zhao H (2006) "Directed evolution of enzymes and biosynthetic pathways." Curr. Opin. Microbiol. 9, 261-267.

Krasnow M A, Cozzarelli N R (1983) "Site-specific relaxation and recombination by the Tn3 resolvase: Recognition of the DNA path between oriented res sites." Cell 32, 1313-1324.

Kulkosky J, Bray S (2006) "HAART-persistent HIV-1 latent reservoirs: their origin, mechanisms of stability and potential strategies for eradication." Cuff. HIV Res. 4, 199-208.

Lalezari J P, Henry K, O'Hearn M, Montaner J S, Piliero P J, Trottier B, Walmsley S, Cohen C, Kuritzkes D R, Eron Jr. J J, Chung J, DeMasi R, Donatacci L, Drobnes C, Delehanty J, Salgo M (2003) "Enfuvirtide, an HIV-1 fusion inhibitor, for drug-resistant HIV infection in North and South America." N. Engl. J. Med. 348, 2175-2185.

Lee Y S, Park J S (1998) "A novel mutant lox? containing part of long terminal repeat of HIV-1 in spacer region: presentation of possible target site for antiviral strategy using site-specific recombinase." Biochem. Biophys. Res. Comm. 253, 588-593.

Lee Y S, Kim S T, Kim G W, Lee M, Park J S (2000) "An engineered lox sequence containing part of a long terminal repeat of HIV-1 permits Cre recombinase-mediated DNA excision." Biochem. Cell Biol. 78, 653-658.

Lehrman G, Hogue I B, Palmer S, Jennings C, Spina C A, Wiegand A, Landay A L, Coombs R W, Richman D D, Mellors J W, Coffin J M, Bosch R J, Margolis D M (2005) "Depletion of latent HIV-1 infection in vivo: a proof-of-concept study" Lancet 366, 549-555.

Lewandoski, M. (2001) "Conditional control of gene expression in the mouse." Nat. Rev. Genet. 2, 743-755.

Lin Q, Jo D, Gebre-Amlak K D, Ruley H E (2004) "Enhanced cell-permeant Cre protein for site-specific recombination in cultured cells." BMC Biotechnol. 4, 25.

Little S J, Holte S, Routy J P, Daar E S, Markowitz M, Collier A C, Koup R A, Mellors J W, Connick E, Conway B, Kilby M, Wang L, Whitcomb J M, Hellmann N S, Richman D D (2002) "Antiretroviral-drug resistance among patients recently infected with HIV." N. Engl. J. Med. 347, 385-394.

Loonstra A, Vooijs M, Beverloo H B, Allak B A, van Drunen E, Kanaar R, Berns A, Jonkers J (2001) "Growth inhibition and DNA damage induced by Cre recombinase in mammalian cells." PNAS 98, 9209-9214.

Macara I G (2001) "Transport into and out of the nucleus." Microbiology and molecular biology reviews 65, 570-594.

Malim M H, Hauber J, Fenrick R, Cullen B R (1988) "Immunodeficiency virus rev trans-activator modulates the expression of the viral regulatory genes." Nature 335, 181-183.

Marcello A (2006) "Latency: the hidden HIV-1 challenge." Retrovirology 3, 7.

Matsumura I, Ellington A D (2001) "In vitro evolution of beta-glucuronidase into a beta-galactosidase proceeds through non-specific intermediates." J. Mol. Biol. 305, 331-339.

Minshull J, Stemmer W P. (1999) "Protein evolution by molecular breeding." Curr. Opin. Chem. Biol. 3, 284-290.

Nagy A (2000) "Cre recombinase: the universal reagent for genome tailoring." Genesis 26, 99-109.

Needleman S B, Wunsch C D (1970) "A general method applicable to the search for similarities in the amino acid sequence of two proteins." J. Mol. Biol. 48, 443-453.

Nolden L, Edenhofer F, Haupt S, Koch P, Wunderlich F T, Siemen H, Brustle O. (2006) "Site-specific recombination in human embryonic stem cells induced by cell-permeant Cre recombinase." Nat. Methods 3, 461-467.

Oess S, Hildt E., Novel cell permeable motif derived from the PreS2-domain of hepatitis-B virus surface antigens, Gene Ther. 2000 May; 7(9):750-8

O'Doherty U, Swiggard W J, Malim M H (2000) "Human immunodeficiency virus type 1 spinoculation enhances infection through virus binding." J Virol. 74, 10074-10080.

Pearson W R, Lipman D J (1988) "Improved tools for biological sequence comparison." Proc Natl Acad Sci USA 85, 2444-2448.

Peitz M, Pfannkuche K, Rajewsky K, Edenhofer F. (2002) "Ability of the hydrophobic FGF and basic TAT peptides to promote cellular uptake of recombinant Cre recombinase: A tool for efficient genetic engineering of mammalian genomes." Proc. Natl. Acad. Sci. USA 99, 4489-4494.

Ratner L, Starcich B, Josephs S F, Hahn B H, Reddy E P, Livak K J, Petteway S R, Jr., Pearson M L, Haseltine W A, Arya S K, (1985) "Polymorphism of the 3' open reading frame of the virus associated with the acquired immune deficiency syndrome, human T-lymphotropic virus type III." Nucl. Acids Res. 13, 8219-8229.

Richard J P, Melikov K, Brooks H, Prevot P, Lebleu B, Chemomordik L V (2005) "Cellular uptake of the unconjugated TAT peptide involves clathrin-dependent endocytosis and heparin sulfate receptors." J. Biol. Chem. 280, 15300-15306.

Rufer A W, Sauer B (2002) "Non-contact positions impose site selectivity on Cre recombinase." Nucl. Acids Res. 30, 2764-2771.

Ruhl M, Himmelspach M, Bahr G M, Hammerschmid F, Jaksche H, Wolff B, Aschauer H, Farrington G K, Probst H, Bevec D, Hauber J (1993) "Eukaryotic initiation factor 5 A is a cellular target of the human immunodeficiency virus type 1 Rev activation domain mediating transactivation" J Cell Biol. 123, 1309-1320.

Sanger F, Nickler S, Coulson A R (1977) "DNA sequencing with chain-terminating inhibitors." Proc. Natl. Acad. Sci. USA 74, 5463-5467.

Santoro S W, Schultz P G (2002) "Directed evolution of the site specificity of Cre recombinase." Proc. Natl. Acad. Sci. USA 99, 4185-4190.

Saraf-Levy T, Santoro S W, Volpin H, Kushnirsky T, Eyal Y, Schultz P G, Gidoni D, Carmi N (2006) "Site-specific recombination of asymmetric lox sites mediated by a heterotetrameric Cre recombinase complex." Bioorg. Med. Chem. 14, 3081-3089.

Sauer B, McDermott J (2004) "DNA recombination with a heterospecific Cre homolog identified from comparison of the pac-c1 regions of P1-related phages." Nucl. Acids. Res. 32, 6086-6095.

Schambach A, Bohne J, Chandra S, Will E, Margison G P, Williams D A, Baum C (2006) "Equal potency of gammaretro viral and *lenti* viral SIN vectors for expression of $O_6$-methylguanine-DNA methyltransferase in hematoietic cells." Molecular Therapy 13, 391-400.

Scherr M, Eder M (2002) "Gene Transfer into Hematopoietic Stem Cells Using Lentiviral Vectors." Current Gene Therapy 2, 45-55.

Shehu-Xhilaga M, Tachedjian G, Crowe S M, Kedzierska K. (2005) "Antiretro viral compounds: mechanisms underlying failure of HAART to eradicate HIV-1." Curr. Med. Chem. 12, 1705-1719.

Shimshek D R, Kim J, Hubner M R, Spergel D J, Buchholz F, Casanova E, Stewart A F, See-burg P H, Sprengel R (2002) "Codon-improved Cre recombinase (iCre) expression in the mouse." Genesis 32(1), 19-26.

Smith T f, Waterman M S (1981) "Overlapping genes and information theory." J Theor. Biol. 91, 379-380.

Stark W M, Boocock M R, Sherratt D J (1992) "Catalysis by site-specific recombinases." Trends Genet. 8, 432-439.

Stemmer WPC (1994) "Rapid evolution of a protein in vitro by DNA shuffling." Nature 370, 389-391.

Sternberg N, Hamilton D (1981) "Bacteriophage P I site-specific recombination. I. Recombination between loxP sites." J. Mol. Biol. 150, 467-486.

Van Duyne G D (2001) "A structural view of cre-loxp site-specific recombination." Annu. Rev. Biophys. Biomol. Struct. 30, 87-104.

Vives E, Brodin P, Lebleu B (1997) "A truncated HIV-1 Tat protein basic domain rapidly translocates through the plasma membrane and accumulates in the cell nucleus." J. Biol. Chem. 272, 16010-16017.

Vives E (2003) "Cellular uptake of the TAT peptide: an endocytosis mechanism following<″> ionic interactions." J. Mol. Recognit. 16, 265-271.

Volkert F C, Broach J R (1986) "Site-specific recombination promotes plasmid amplification in yeast." Cell 46, 541-550.

Voziyanov Y, Konieczka J H, Stewart A F, Jayaram M (2003) "Stepwise manipulation of DNA specificity in Flp recombinase: progressively adapting Flp to individual and combinatorial mutations in its target site." J. Mol. Biol. 326, 65-76.

Yuan L, Kurek I, English J, Keenan R (2005) "Laboratory-directed protein evolution" Microbiol. Mol. Biol. Rev. 69, 373-92.

WO 2002/44409
WO 2008/083931
WO 2011/147590.

---

The invention claimed is:

1. A nucleic acid encoding a tailored recombinase, which tailored recombinase is capable of recombining the asymmetric target sequence SEQ ID NO:1 within the long terminal repeat (LTR) of proviral DNA of a plurality of HIV-1 strains, wherein the amino acid sequence of the tailored recombinase has at least 95% sequence identity to SEQ ID NO:10, wherein said tailored recombinase comprises all of the following defined amino acid exchanges as compared to SEQ ID NO:6: V7L, P12S, P15L, M30V, H40R, M44V, S51T, Y77H, K86N, Q89L, G93A, S108G, C155G, A175S, A249V, R259D, E262R, T268A, D278G, P307A, N317T, and I320S.

2. The nucleic acid according to claim 1, wherein the tailored recombinase comprises the amino acid sequence of SEQ ID NO:10.

3. The nucleic acid according to claim 1, wherein the tailored recombinase comprises the amino acid sequence of SEQ ID NO:11, 12, or 13.

4. The nucleic acid of claim 1, wherein the tailored recombinase does not recombine loxP (SEQ ID NO:4) or loxH (SEQ ID NO:5) sequences with detectable activity.

5. A transformed cell comprising the nucleic acid of claim 1.

6. A pharmaceutical composition comprising the nucleic acid of claim 1.

7. The pharmaceutical composition of claim 6, wherein the pharmaceutical composition is for use in treatment or prevention of retrovirus infection in a subject, wherein the retrovirus is HIV, and wherein the pharmaceutical composition is optionally formulated for administration to a subject, if proviral DNA found in a sample obtained from the subject comprises the asymmetric target sequence identified in step (a) on which the recombinase has been selected.

8. A method for preparing a tailored recombinase, comprising: expressing the tailored recombinase from the nucleic acid of claim 1 inserted into an expression vector in a suitable host cell, wherein the recombinase is optionally expressed as a fusion polypeptide comprising the amino acid sequence of the tailored recombinase.

9. A method for preparing a transformed cell, comprising: introducing an expression vector that comprises the nucleic acid of claim 1 into a cell in vitro.

10. A pharmaceutical composition comprising a transformed cell according to claim 5.

11. The nucleic acid of claim 1, wherein the amino acid sequence of the tailored recombinase has at least 99% sequence identity to SEQ ID NO:10.

12. The method of claim 9, wherein the cell is an adult stem cell.

13. The transformed cell of claim 5, where the cell is a stem cell from the hematopoietic lineage.

14. A tailored recombinase encoded by the nucleic acid of claim 1.

15. The tailored recombinase of claim 14, wherein the tailored recombinase is expressed as a fusion protein.

16. A pharmaceutical composition comprising a tailored recombinase according to claim 14.

17. The pharmaceutical composition of claim 7, wherein the retrovirus is HIV-1.

* * * * *

SEQUENCE LISTING

```
<160> NUMBER OF SEQ ID NOS: 14

<210> SEQ ID NO 1
<211> LENGTH: 34
<212> TYPE: DNA
<213> ORGANISM: Human immunodeficiency virus 1

<400> SEQUENCE: 1
aacccactgc ttaagcctca ataaagcttg cctt                              34

<210> SEQ ID NO 2
<211> LENGTH: 34
<212> TYPE: DNA
<213> ORGANISM: Human immunodeficiency virus 1

<400> SEQUENCE: 2
ctgggcggga ctggggagtg gcgagccctc agat                              34

<210> SEQ ID NO 3
<211> LENGTH: 34
<212> TYPE: DNA
<213> ORGANISM: Human immunodeficiency virus 1

<400> SEQUENCE: 3
acaacatcct attacaccct atatgccaac atgg                              34

<210> SEQ ID NO 4
<211> LENGTH: 34
<212> TYPE: DNA
<213> ORGANISM: Artificial Sequence
<220> FEATURE:
<223> OTHER INFORMATION: Synthetic sequence

<400> SEQUENCE: 4
ataacttcgt ataatgtatg ctatacgaag ttat                              34

<210> SEQ ID NO 5
<211> LENGTH: 34
<212> TYPE: DNA
<213> ORGANISM: Artificial Sequence
<220> FEATURE:
<223> OTHER INFORMATION: Synthetic sequence

<400> SEQUENCE: 5
atatatacgt atatagacat atatacgtat atat                              34

<210> SEQ ID NO 6
<211> LENGTH: 343
<212> TYPE: PRT
<213> ORGANISM: Enterobacteria phage P1
```

<400> SEQUENCE: 6

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

<210> SEQ ID NO 7
<211> LENGTH: 343
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (1)...(343)

<223> OTHER INFORMATION: Xaa = Any Amino Acid

<400> SEQUENCE: 7

Met Ser Xaa Xaa Xaa Thr Xaa Xaa Xaa Leu Xaa Ala Leu Xaa Xaa
1               5                   10                  15

Asp Xaa Xaa Ser Asp Xaa Xaa Xaa Xaa Leu Xaa Xaa Xaa Xaa Arg
            20                  25                  30

Asp Xaa Xaa Ala Xaa Ser Xaa Xaa Thr Trp Xaa Xaa Leu Leu Ser Xaa
            35                  40                  45

Cys Arg Xaa Trp Xaa Ala Trp Cys Xaa Xaa Xaa Xaa Arg Xaa Xaa Phe
        50                  55                  60

Pro Xaa Xaa Pro Xaa Xaa Val Arg Xaa Tyr Leu Xaa Leu Gln Xaa
65                  70                  75                  80

Arg Gly Leu Xaa Val Xaa Thr Xaa Gln Gln His Leu Xaa Xaa Leu Asn
                85                  90                  95

Met Xaa His Arg Arg Xaa Gly Leu Xaa Arg Xaa Xaa Asp Xaa Xaa Xaa
        100                 105                 110

Val Ser Leu Xaa Xaa Arg Arg Ile Arg Xaa Glu Asn Val Asp Ala Gly
            115                 120                 125

Glu Arg Xaa Lys Gln Ala Leu Ala Phe Xaa Arg Xaa Asp Xaa Xaa Xaa
130                 135                 140

Xaa Xaa Xaa Leu Xaa Xaa Xaa Ser Xaa Xaa Xaa Xaa Asp Xaa Arg Xaa
145                 150                 155                 160

Leu Ala Xaa Leu Gly Xaa Ala Tyr Asn Thr Leu Leu Arg Xaa Xaa Glu
            165                 170                 175

Xaa Xaa Xaa Xaa Arg Xaa Xaa Asp Xaa Ser Xaa Thr Xaa Gly Gly Arg
            180                 185                 190

Xaa Leu Ile His Xaa Xaa Xaa Thr Lys Thr Leu Val Ser Thr Xaa Gly
            195                 200                 205

Val Glu Lys Ala Leu Ser Leu Xaa Xaa Thr Xaa Leu Xaa Glu Arg Trp
210                 215                 220

Xaa Ser Xaa Ser Gly Val Ala Xaa Xaa Xaa Xaa Xaa Tyr Leu Phe Cys
225                 230                 235                 240

Xaa Xaa Xaa Xaa Xaa Gly Xaa Ala Xaa Pro Xaa Ala Xaa Xaa Xaa Leu
            245                 250                 255

Ser Xaa Xaa Xaa Leu Xaa Xaa Ile Phe Xaa Xaa Xaa His Xaa Xaa Xaa
            260                 265                 270

Xaa Gly Ala Lys Xaa Xaa Ser Gly Xaa Arg Tyr Xaa Xaa Trp Ser Gly
        275                 280                 285

His Ser Ala Arg Val Gly Ala Ala Arg Asp Met Ala Arg Ala Gly Val
        290                 295                 300

Xaa Ile Xaa Glu Ile Met Gln Ala Gly Gly Trp Xaa Thr Val Xaa Xaa
305                 310                 315                 320

Val Met Asn Tyr Ile Arg Asn Leu Asp Ser Glu Xaa Gly Ala Met Val
            325                 330                 335

Arg Leu Leu Glu Xaa Xaa Xaa
        340

<210> SEQ ID NO 8
<211> LENGTH: 343
<212> TYPE: PRT
<213> ORGANISM: Artificial Sequence
<220> FEATURE:
<223> OTHER INFORMATION: Synthetic sequence
<220> FEATURE:
<221> NAME/KEY: VARIANT
<222> LOCATION: (1)...(343)
<223> OTHER INFORMATION: Xaa = Any Amino Acid

<400> SEQUENCE: 8

```
Met Ser Xaa Xaa Xaa Thr Xaa Xaa Xaa Leu Ser Ala Leu Leu Xaa
1               5                   10                  15

Asp Xaa Xaa Ser Asp Xaa Xaa Xaa Xaa Leu Xaa Xaa Xaa Xaa Arg
            20                  25                  30

Asp Xaa Xaa Ala Xaa Ser Xaa Xaa Thr Trp Xaa Val Leu Leu Ser Xaa
        35                  40                  45

Cys Arg Xaa Trp Xaa Ala Trp Cys Xaa Xaa Xaa Arg Xaa Xaa Phe
    50                  55                  60

Pro Xaa Xaa Pro Xaa Xaa Val Arg Xaa Tyr Leu Leu Xaa Leu Gln Xaa
65              70                  75                  80

Arg Gly Leu Xaa Val Asn Thr Xaa Gln Gln His Leu Ala Xaa Leu Asn
            85                  90                  95

Met Xaa His Arg Arg Xaa Gly Leu Xaa Arg Xaa Xaa Asp Ser Xaa Xaa
        100                 105                 110

Val Ser Leu Xaa Xaa Arg Arg Ile Arg Xaa Glu Asn Val Asp Ala Gly
    115                 120                 125

Glu Arg Xaa Lys Gln Ala Leu Ala Phe Xaa Arg Xaa Asp Xaa Xaa
        130                 135                 140

Xaa Xaa Xaa Leu Xaa Xaa Xaa Ser Xaa Xaa Xaa Xaa Asp Xaa Arg Xaa
145                 150                 155                 160

Leu Ala Xaa Leu Gly Xaa Ala Tyr Asn Thr Leu Leu Arg Xaa Ser Glu
            165                 170                 175

Xaa Xaa Xaa Xaa Arg Xaa Xaa Asp Xaa Ser Xaa Thr Xaa Gly Gly Arg
        180                 185                 190

Xaa Leu Ile His Xaa Xaa Xaa Thr Lys Thr Leu Val Ser Thr Xaa Gly
            195                 200                 205

Val Glu Lys Ala Leu Ser Leu Xaa Xaa Thr Xaa Leu Xaa Glu Arg Trp
    210                 215                 220

Xaa Ser Xaa Ser Gly Val Ala Xaa Xaa Xaa Xaa Tyr Leu Phe Cys
225                 230                 235                 240

Xaa Xaa Xaa Xaa Xaa Gly Xaa Ala Xaa Pro Xaa Ala Xaa Xaa Xaa Leu
            245                 250                 255

Ser Xaa Xaa Xaa Leu Xaa Xaa Ile Phe Xaa Xaa Xaa His Xaa Xaa Xaa
        260                 265                 270

Xaa Gly Ala Lys Xaa Xaa Ser Gly Xaa Arg Tyr Xaa Xaa Trp Ser Gly
    275                 280                 285

His Ser Ala Arg Val Gly Ala Ala Arg Asp Met Ala Arg Ala Gly Val
290                 295                 300

Xaa Ile Ala Glu Ile Met Gln Ala Gly Gly Trp Xaa Thr Val Xaa Xaa
305                 310                 315                 320

Val Met Asn Tyr Ile Arg Asn Leu Asp Ser Glu Xaa Gly Ala Met Val
            325                 330                 335

Arg Leu Leu Glu Xaa Xaa Xaa
            340
```

<210> SEQ ID NO 9
<211> LENGTH: 343
<212> TYPE: PRT
<213> ORGANISM: Artificial Sequence
<220> FEATURE:
<223> OTHER INFORMATION: synthetic sequence
<220> FEATURE:

<221> NAME/KEY: VARIANT
<222> LOCATION: (1)...(343)
<223> OTHER INFORMATION: Xaa = Any Amino Acid

<400> SEQUENCE: 9

Met Ser Xaa Xaa Xaa Thr Leu Xaa Xaa Xaa Leu Ser Ala Leu Leu Xaa
1               5                   10                  15

Asp Xaa Xaa Ser Asp Xaa Xaa Xaa Xaa Leu Xaa Xaa Val Xaa Arg
            20                  25                  30

Asp Xaa Xaa Ala Xaa Ser Xaa Arg Thr Trp Xaa Val Leu Leu Ser Xaa
            35                  40                  45

Cys Arg Thr Trp Xaa Ala Trp Cys Xaa Xaa Xaa Arg Xaa Xaa Phe
50                  55                  60

Pro Xaa Xaa Pro Xaa Xaa Val Arg Xaa Tyr Leu Leu His Leu Gln Xaa
65                  70                  75                  80

Arg Gly Leu Xaa Val Asn Thr Xaa Leu Gln His Leu Ala Xaa Leu Asn
            85                  90                  95

Met Xaa His Arg Arg Xaa Gly Leu Xaa Arg Xaa Gly Asp Ser Xaa Xaa
            100                 105                 110

Val Ser Leu Xaa Xaa Arg Arg Ile Arg Xaa Glu Asn Val Asp Ala Gly
            115                 120                 125

Glu Arg Xaa Lys Gln Ala Leu Ala Phe Xaa Arg Xaa Asp Xaa Xaa
            130                 135                 140

Xaa Xaa Xaa Leu Xaa Xaa Xaa Ser Xaa Xaa Gly Xaa Asp Xaa Arg Thr
145                 150                 155                 160

Leu Ala Xaa Leu Gly Xaa Ala Tyr Asn Thr Leu Leu Arg Xaa Ser Glu
                165                 170                 175

Xaa Xaa Xaa Xaa Arg Xaa Xaa Asp Xaa Ser Xaa Thr Xaa Gly Gly Arg
            180                 185                 190

Xaa Leu Ile His Xaa Xaa Xaa Thr Lys Thr Leu Val Ser Thr Xaa Gly
            195                 200                 205

Val Glu Lys Ala Leu Ser Leu Xaa Xaa Thr Xaa Leu Xaa Glu Arg Trp
210                 215                 220

Xaa Ser Xaa Ser Gly Val Ala Xaa Xaa Xaa Xaa Tyr Leu Phe Cys
225                 230                 235                 240

Gln Xaa Xaa Ile Xaa Gly Xaa Ala Val Pro Xaa Ala Xaa Xaa Xaa Leu
                245                 250                 255

Ser Xaa Asp Xaa Leu Arg Xaa Ile Phe Xaa Xaa Ala His Xaa Xaa Xaa
            260                 265                 270

Xaa Gly Ala Lys Xaa Gly Ser Gly Xaa Arg Tyr Xaa Xaa Trp Ser Gly
            275                 280                 285

His Ser Ala Arg Val Gly Ala Ala Arg Asp Met Ala Arg Ala Gly Val
            290                 295                 300

Xaa Ile Ala Glu Ile Met Gln Ala Gly Gly Trp Xaa Thr Val Glu Ser
305                 310                 315                 320

Val Met Asn Tyr Ile Arg Asn Leu Asp Ser Xaa Gly Ala Met Val
                325                 330                 335

Arg Leu Leu Glu Xaa Xaa Xaa
            340

<210> SEQ ID NO 10
<211> LENGTH: 343
<212> TYPE: PRT
<213> ORGANISM: Artificial Sequence
<220> FEATURE:
<223> OTHER INFORMATION: synthetic sequence

```
<220> FEATURE:
<221> NAME/KEY: VARIANT
<222> LOCATION: (1)...(343)
<223> OTHER INFORMATION: Xaa = Any Amino Acid

<400> SEQUENCE: 10

Met Ser Xaa Leu Xaa Thr Leu His Gln Xaa Leu Ser Ala Leu Leu Val
1               5                   10                  15

Asp Xaa Xaa Ser Asp Glu Xaa Arg Lys Asn Leu Met Asp Val Leu Arg
            20                  25                  30

Asp Arg Gln Ala Phe Ser Glu Arg Thr Trp Lys Val Leu Leu Ser Val
        35                  40                  45

Cys Arg Thr Trp Ala Ala Trp Cys Xaa Leu Asn Asn Arg Lys Xaa Phe
    50                  55                  60

Pro Ala Glu Pro Glu Asp Val Arg Asp Tyr Leu Leu His Leu Gln Xaa
65                  70                  75                  80

Arg Gly Leu Xaa Val Asn Thr Xaa Leu Gln His Leu Ala Gln Leu Asn
                85                  90                  95

Met Leu His Arg Arg Phe Gly Leu Pro Arg Pro Gly Asp Ser Xaa Ala
            100                 105                 110

Val Ser Leu Val Xaa Arg Arg Ile Arg Arg Glu Asn Val Asp Ala Gly
        115                 120                 125

Glu Arg Thr Lys Gln Ala Leu Ala Phe Glu Arg Thr Asp Phe Asp Gln
130                 135                 140

Val Arg Ala Leu Met Glu Xaa Ser Xaa Arg Gly Gln Asp Ile Arg Xaa
145                 150                 155                 160

Leu Ala Xaa Leu Gly Val Ala Tyr Asn Thr Leu Leu Arg Xaa Ser Glu
                165                 170                 175

Ile Ala Arg Ile Arg Xaa Xaa Asp Ile Ser Arg Thr Asp Gly Gly Arg
            180                 185                 190

Met Leu Ile His Ile Xaa Arg Thr Lys Thr Leu Val Ser Thr Ala Gly
        195                 200                 205

Val Glu Lys Ala Leu Ser Leu Gly Val Thr Xaa Leu Val Glu Arg Trp
210                 215                 220

Ile Ser Val Ser Gly Val Ala Xaa Asp Pro Asn Asn Tyr Leu Phe Cys
225                 230                 235                 240

Xaa Val Arg Xaa Asn Gly Xaa Ala Val Pro Ser Ala Thr Ser Xaa Leu
                245                 250                 255

Ser Thr Asp Val Leu Arg Xaa Ile Phe Xaa Ala Ala His Arg Leu Xaa
            260                 265                 270

Tyr Gly Ala Lys Asp Gly Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Val Xaa Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 11
<211> LENGTH: 343
<212> TYPE: PRT
<213> ORGANISM: Artificial Sequence
<220> FEATURE:
```

<223> OTHER INFORMATION: synthetic sequence

<400> SEQUENCE: 11

```
Met Ser Ile Leu Leu Thr Leu His Gln Ser Leu Ser Ala Leu Leu Val
1               5                   10                  15

Asp Ala Thr Ser Asp Glu Ala Arg Lys Asn Leu Met Asp Val Leu Arg
            20                  25                  30

Asp Arg Gln Ala Phe Ser Glu Arg Thr Trp Lys Val Leu Leu Ser Val
        35                  40                  45

Cys Arg Thr Trp Ala Ala Trp Cys Lys Leu Asn Asn Arg Lys Trp Phe
    50                  55                  60

Pro Ala Glu Pro Glu Asp Val Arg Asp Tyr Leu His Leu Gln Ala
65                  70                  75                  80

Arg Gly Leu Ala Val Asn Thr Ile Leu Gln His Leu Ala Gln Leu Asn
                85                  90                  95

Met Leu His Arg Arg Phe Gly Leu Pro Arg Pro Gly Asp Ser Asp Ala
            100                 105                 110

Val Ser Leu Val Met Arg Arg Ile Arg Arg Glu Asn Val Asp Ala Gly
        115                 120                 125

Glu Arg Thr Lys Gln Ala Leu Ala Phe Glu Arg Thr Asp Phe Asp Gln
    130                 135                 140

Val Arg Ala Leu Met Glu Asn Ser Gly Arg Gly Gln Asp Ile Arg Thr
145                 150                 155                 160

Leu Ala Leu Leu Gly Val Ala Tyr Asn Thr Leu Leu Arg Val Ser Glu
                165                 170                 175

Ile Ala Arg Ile Arg Ile Lys Asp Ile Ser Arg Thr Asp Gly Gly Arg
            180                 185                 190

Met Leu Ile His Ile Ser Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Ser Asp Pro Asn Asn Tyr Leu Phe Cys
225                 230                 235                 240

Gln Val Arg Ile Asn Gly Val Ala Val Pro Ser Ala Thr Ser Arg Leu
                245                 250                 255

Ser Thr Asp Val Leu Arg Lys Ile Phe Glu Ala Ala His Arg Leu Ile
            260                 265                 270

Tyr Gly Ala Lys Asp Gly Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Val Glu Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

<210> SEQ ID NO 12
<211> LENGTH: 343
<212> TYPE: PRT
<213> ORGANISM: Artificial Sequence
<220> FEATURE:
<223> OTHER INFORMATION: synthetic sequence

<400> SEQUENCE: 12

```
Met Ser Ser Leu Gln Thr Leu His Gln Asn Leu Ser Ala Leu Leu Val
1               5                   10                  15

Asp Val Thr Ser Asp Glu Val Arg Lys Asn Leu Met Asp Val Leu Arg
            20                  25                  30

Asp Arg Gln Ala Phe Ser Glu Arg Thr Trp Lys Val Leu Leu Ser Val
        35                  40                  45

Cys Arg Thr Trp Ala Ala Trp Cys Lys Leu Asn Asn Arg Lys Arg Phe
    50                  55                  60

Pro Ala Glu Pro Glu Asp Val Arg Asp Tyr Leu Leu His Leu Gln Thr
65                  70                  75                  80

Arg Gly Leu Thr Val Asn Thr Ile Leu Gln His Leu Ala Gln Leu Asn
                85                  90                  95

Met Leu His Arg Arg Phe Gly Leu Pro Arg Pro Gly Asp Ser Asp Ala
            100                 105                 110

Val Ser Leu Val Ile Arg Arg Ile Arg Arg Glu Asn Val Asp Ala Gly
        115                 120                 125

Glu Arg Thr Lys Gln Ala Leu Ala Phe Glu Arg Thr Asp Phe Asp Gln
    130                 135                 140

Val Arg Ala Leu Met Glu Asn Ser Asp Arg Gly Gln Asp Ile Arg Ser
145                 150                 155                 160

Leu Ala Phe Leu Gly Val Ala Tyr Asn Thr Leu Leu Arg Ile Ser Glu
                165                 170                 175

Ile Ala Arg Ile Arg Val Arg Asp Ile Ser Arg Thr Asp Gly Gly Arg
            180                 185                 190

Met Leu Ile His Ile Ser Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Pro Val Arg Val Asn Gly Ala Ala Val Pro Ser Ala Thr Ser Gln Leu
                245                 250                 255

Ser Thr Asp Val Leu Arg Gly Ile Phe Glu Ala Ala His Arg Leu Val
            260                 265                 270

Tyr Gly Ala Lys Asp Gly Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Ala Glu Ile Met Gln Ala Gly Gly Trp Thr Thr Val Glu Ser
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

<210> SEQ ID NO 13
<211> LENGTH: 343
<212> TYPE: PRT
<213> ORGANISM: Artificial Sequence
<220> FEATURE:
<223> OTHER INFORMATION: synthetic sequence

<400> SEQUENCE: 13

```
Met Ser Ser Leu Leu Thr Leu His Gln Ser Leu Ser Ala Leu Leu Val
1               5                   10                  15
```

Asp Val Ala Ser Asp Glu Ala Arg Lys Asn Leu Met Asp Val Leu Arg
            20                  25                  30

Asp Arg Gln Ala Phe Ser Glu Arg Thr Trp Lys Val Leu Ser Val
        35                  40                  45

Cys Arg Thr Trp Ala Ala Trp Cys Glu Leu Asn Asn Arg Lys Arg Phe
50                  55                  60

Pro Ala Glu Pro Glu Asp Val Arg Asp Tyr Leu Leu His Leu Gln Thr
65                  70                  75                  80

Arg Gly Leu Thr Val Asn Thr Val Leu Gln His Leu Ala Gln Leu Asn
                85                  90                  95

Met Leu His Arg Arg Phe Gly Leu Pro Arg Pro Gly Asp Ser Asn Ala
            100                 105                 110

Val Ser Leu Val Ile Arg Arg Ile Arg Arg Glu Asn Val Asp Ala Gly
        115                 120                 125

Glu Arg Thr Lys Gln Ala Leu Ala Phe Glu Arg Thr Asp Phe Asp Gln
130                 135                 140

Val Arg Ala Leu Met Glu Asp Ser Asp Arg Gly Gln Asp Ile Arg Ser
145                 150                 155                 160

Leu Ala Phe Leu Gly Val Ala Tyr Asn Thr Leu Leu Arg Ile Ser Glu
                165                 170                 175

Ile Ala Arg Ile Arg Val Arg Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Glu Leu Val Glu Arg Trp
210                 215                 220

Ile Ser Val Ser Gly Val Ala Asp Asp Pro Asn Asn Tyr Leu Phe Cys
225                 230                 235                 240

Gln Val Arg Ile Asn Gly Val Ala Val Pro Ser Ala Thr Ser Gln Leu
                245                 250                 255

Ser Thr Asp Val Leu Arg Gly Ile Phe Ala Ala His Arg Leu Ile
            260                 265                 270

Tyr Gly Ala Lys Asp Gly Ser Gly Gln Arg Tyr Leu Ala Trp Ser Gly
        275                 280                 285

His Ser Ala Arg Val Gly Ala Ala Arg Asp Met Ala Arg Ala Gly Val
290                 295                 300

Ser Ile Ala Glu Ile Met Gln Ala Gly Gly Trp Thr Thr Val Asp Ser
305                 310                 315                 320

Val Met Asn Tyr Ile Arg Asn Leu Asp Ser Glu Thr Gly Ala Met Val
                325                 330                 335

Arg Leu Leu Glu Asp Ser Asp
            340

<210> SEQ ID NO 14
<211> LENGTH: 351
<212> TYPE: PRT
<213> ORGANISM: Artificial Sequence
<220> FEATURE:
<223> OTHER INFORMATION: synthetic sequence

<400> SEQUENCE: 14

Met Val Pro Lys Lys Lys Arg Lys Val Ser Ile Leu Leu Thr Leu His
1               5                   10                  15

Gln Ser Leu Ser Ala Leu Leu Val Asp Ala Thr Ser Asp Glu Ala Arg
            20                  25                  30

```
Lys Asn Leu Met Asp Val Leu Arg Asp Arg Gln Ala Phe Ser Glu Arg
        35              40                  45
Thr Trp Lys Val Leu Leu Ser Val Cys Arg Thr Trp Ala Ala Trp Cys
        50              55                  60
Lys Leu Asn Asn Arg Lys Trp Phe Pro Ala Glu Pro Glu Asp Val Arg
65              70                  75                      80
Asp Tyr Leu Leu His Leu Gln Ala Arg Gly Leu Ala Val Asn Thr Ile
                85                  90                  95
Leu Gln His Leu Ala Gln Leu Asn Met Leu His Arg Arg Phe Gly Leu
            100             105                 110
Pro Arg Pro Gly Asp Ser Asp Ala Val Ser Leu Val Met Arg Arg Ile
        115             120                 125
Arg Arg Glu Asn Val Asp Ala Gly Glu Arg Thr Lys Gln Ala Leu Ala
130             135                 140
Phe Glu Arg Thr Asp Phe Asp Gln Val Arg Ala Leu Met Glu Asn Ser
145             150                 155                     160
Glu Arg Gly Gln Asp Ile Arg Thr Leu Ala Leu Leu Gly Val Ala Tyr
                165             170                 175
Asn Thr Leu Leu Arg Val Ser Glu Ile Ala Arg Ile Arg Ile Lys Asp
            180                 185                 190
Ile Ser Arg Thr Asp Gly Gly Arg Met Leu Ile His Ile Ser Arg Thr
            195             200                 205
Lys Thr Leu Val Ser Thr Ala Gly Val Glu Lys Ala Leu Ser Leu Gly
        210             215                 220
Val Thr Lys Leu Val Glu Arg Trp Ile Ser Val Ser Gly Val Ala Ser
225             230                 235                     240
Asp Pro Asn Asn Tyr Leu Phe Cys Gln Val Arg Ile Asn Gly Val Ala
                245                 250                 255
Val Pro Ser Ala Thr Ser Arg Leu Ser Thr Asp Val Leu Arg Lys Ile
            260             265                 270
Phe Glu Ala Ala His Arg Leu Ile Tyr Gly Ala Lys Asp Gly Ser Gly
        275             280                 285
Gln Arg Tyr Leu Ala Trp Ser Gly His Ser Ala Arg Val Gly Ala Ala
        290             295                 300
Arg Asp Met Ala Arg Ala Gly Val Ser Ile Ala Glu Ile Met Gln Ala
305             310                 315                     320
Gly Gly Trp Thr Thr Val Glu Ser Val Met Asn Tyr Ile Arg Asn Leu
                325             330                 335
Asp Ser Glu Thr Gly Ala Met Val Arg Leu Leu Glu Asp Gly Asp
            340             345                 350
```